US007473821B2

(12) United States Patent
Abad et al.

(10) Patent No.: US 7,473,821 B2
(45) Date of Patent: Jan. 6, 2009

(54) NUCLEIC ACIDS ENCODING CRY8BB1 ENDOTOXINS ENGINEERED TO HAVE INSECT-SPECIFIC PROTEASE RECOGNITION SEQUENCES

(75) Inventors: Andre R. Abad, W. Des Moines, IA (US); Gary C. Chun, Newark, DE (US); Ronald D. Flannagan, Grimes, IA (US); Rafael Herrmann, Wilmington, DE (US); Albert L. Lu, Newark, DE (US); Janet A. Rice, Wilmington, DE (US); Eric J. Schepers, Port Deposit, MD (US)

(73) Assignees: Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 126 days.

(21) Appl. No.: 11/448,266

(22) Filed: Jun. 7, 2006

(65) Prior Publication Data
US 2006/0288448 A1 Dec. 21, 2006

Related U.S. Application Data

(60) Provisional application No. 60/688,635, filed on Jun. 8, 2005, provisional application No. 60/722,787, filed on Sep. 30, 2005.

(51) Int. Cl.
*A01H 5/00* (2006.01)
*A01H 5/10* (2006.01)
*C12N 15/82* (2006.01)
*C12N 15/32* (2006.01)

(52) U.S. Cl. ............... 800/302; 800/279; 536/23.71
(58) Field of Classification Search ............... None
See application file for complete search history.

(56) References Cited

U.S. PATENT DOCUMENTS

| 2003/0120054 A1 | 6/2003 | Chen et al. |
| 2005/0166284 A1 | 7/2005 | Abad et al. |

FOREIGN PATENT DOCUMENTS

| WO | WO 02/34774 A2 | | 5/2002 |
| WO | WO03/018810 | * | 3/2003 |
| WO | WO 04/003148 A2 | | 1/2004 |
| WO | WO 2004/00314 | * | 1/2004 |
| WO | WO 05/063996 A2 | | 7/2005 |
| WO | WO 05/066349 A2 | | 7/2005 |

OTHER PUBLICATIONS

Guo et al (2004, Proc. Natl. Acad. Sci. USA 101: 9205-9210).*
Aaronson et al (2001, FEMS Microbiol. Lett. 195:1-8).*
Tounsi et al, 2003, J. Appl. Microbiol. 95:23-28.*
de Maagd et al, 1999, Appl. Environ. Microbiol. 65:4369-4374.*
de Maagd et al (2001, Trends Genet. 17:193-199).*
Crickmore, N., et al. "Revision of the Nomenclature for the Bacillus Thuringiensis Pesticidal Crystal Proteins," *Microbiology and Molecular Biology Reviews*, 1998, pp. 807-813, vol. 62(3).
Oppert, B., "Protease Interactions With Bacillus Thuringiensis Insecticidal Toxins," *Archives of Insect Biochemistry and Physiology*, 1999, pp. 1-12, vol. 42(1).
Rukmini, et al., "Bacillus Thurigiensis Crystal Delta-Endotoxin: Role of Proteases in the Conversion of Protoxin to Toxin," *Biochimie*, 2000, pp. 109-116, vol. 82.
Schnepf, E., et al., "Bacillus Thuringiensis and Its Pesticidal Crystal Proteins," *Microbiology*, 1998, pp. 775-806, vol. 62(3).
Bown, D.P., et al., "Characterisation of Cysteine Proteinases Responsible for Digestive Proteolysis in Guts of Larval Western Corn Rootworm (*Diabrotica Virgifera*) by Expression in the Yeast Pichia Pastoris," *Insect Biochemistry and Molecular Biology*, 2004, pp. 305-320, vol. 34.
Koiwa, H., et al., "A Plant Defensive Cystatin (soyacystatin) Targets Cathepsin L-Like Digestive Cysteine Proteinases (DvCALs) in the Larval Midgut of Western Corn Rootworm (*Diabrotica Virgifera Virgifera*)," 2000, pp. 67-70, vol. 471.
Koiwa, H. et al., "An In-Gel Assay of A Recombinant Western Corn Rootworm (*Diabrotica Virgifera Virgifera*) Cysteine Proteinase Expressed in Yeast," 2000, pp. 153-155, vol. 282.

* cited by examiner

Primary Examiner—Anne R Kubelik
(74) Attorney, Agent, or Firm—Alston & Bird LLP

(57) ABSTRACT

Compositions and methods for protecting a plant from an insect pest are provided. Nucleic acid molecules encoding insect protoxins or insect toxins modified to comprise at least one proteolytic activation site that is sensitive to an insect gut protease are provided. Cleavage of a modified insect protoxin at the proteolytic activation site by an insect gut protease produces an active insect toxin in the gut of the insect pest. Cleavage of a modified insect toxin of the invention at a proteolytic activation site results in the production of an active insect toxin in the insect gut that displays improved pesticidal activity relative to the insect toxin that lacks the proteolytic activation site. Methods of using the modified insect protoxin and modified insect toxin nucleic acid sequences and the polypeptides they encode to protect a plant from an insect pest are provided. Particular embodiments of the invention further provide modified insect protoxin and modified insect toxin compositions and formulations, expression cassettes, and transformed plants, plant cells, and seeds. Insect gut proteases and the nucleic acid molecules that encode them are also disclosed herein.

23 Claims, No Drawings

NUCLEIC ACIDS ENCODING CRY8BB1 ENDOTOXINS ENGINEERED TO HAVE INSECT-SPECIFIC PROTEASE RECOGNITION SEQUENCES

CROSS REFERENCE TO RELATED APPLICATIONS

This application claims the benefit of U.S. Provisional Application Ser. No. 60/688,635, filed Jun. 8, 2005 and U.S. Provisional Application Ser. No. 60/722,787, filed Sep. 30, 2005, both of which are incorporated herein by reference in their entirety.

FIELD OF THE INVENTION

The present invention relates to the fields of plant molecular biology and plant pest control.

BACKGROUND OF THE INVENTION

Insect pests are a major factor in the loss of the world's agricultural crops. For example, corn rootworm feeding damage or boll weevil damage can be economically devastating to agricultural producers. Insect pest-related crop loss from corn rootworm alone has reached one billion dollars a year.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative. Generally speaking, the use of biopesticides presents a lower risk of pollution and environmental hazards, and provides greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including *Lepidoptera, Diptera, Coleoptera, Hemiptera*, and others. *Bacillus thuringiensis* and *Bacillus papilliae* are among the most successful biocontrol agents discovered to date. Insect pathogenicity has been attributed to strains of: *B. larvae, B. lentimorbus, B. papilliae, B. sphaericus, B. thuringiensis* (Harwook, ed. (1989) *Bacillus* (Plenum Press), p. 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial pesticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants genetically engineered to produce pesticidal proteins isolated from strains of *B. thuringiensis*, known as δ-endotoxins or Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been sold to the American farmer. However, while they have proven to be very successful commercially, these genetically engineered, insect-resistant crop plants provide resistance to only a narrow range of the economically important insect pests. Some insects, such as Western corn rootworm, have proven to be recalcitrant.

Accordingly, efforts have been made to understand the mechanism of action of Bt toxins and to engineer toxins with improved properties. It has been shown that insect gut proteases can affect the impact of *Bacillus thuringiensis* Cry proteins and other pesticidal proteins on the insect. Some proteases activate Cry proteins by processing them from a "protoxin" form into a toxic form, or "toxin." See, Oppert (1999) *Arch. Insect Biochem. Phys.* 42:1-12 and Carroll et al. (1997) *J. Invertebrate Pathology* 70:41-49. This activation of the toxin can include the removal of the N- and C-terminal peptides from the protein and can also include internal cleavage of the protein. Other proteases can degrade pesticidal proteins. See Oppert, ibid.; see also U.S. Pat. Nos. 6,057,491 and 6,339,491.

Researchers have determined that plants express a variety of proteases, including serine and cysteine proteases. See, for example, Goodfellow et al. (1993) *Plant Physiol.* 101:415-419; Pechan et al. (1999) *Plant Mol. Biol.* 40:111-119; Lid et al. (2002) *Proc. Nat. Acad. Sci. USA* 99:5460-5465. Research has also shown that insect gut proteases include cathepsins, such as cathepsin B- and L-like proteinases. See, Shiba et al. (2001) *Arch. Biochem. Biophys.* 390:28-34; see also, Purcell et al. (1992) *Insect Biochem. Mol. Biol.* 22:41-47. For example, cathepsin L-like digestive cysteine proteinases are found in the larval midgut of Western corn rootworm. See, Koiwa et al. (2000) *FEBS Letters* 471:67-70; see also, Koiwa et al. (2000) *Analytical Biochemistry* 282:153-155. The preferred proteolytic substrate sites of these proteases have been investigated using synthetic substrates. See, Alves et al. (2001) *Eur. J. Biochem.* 268:1206-1212 and Melo et al. (2001) *Anal. Biochem.* 293:71-77.

While investigators have previously genetically engineered plants, particularly crop plants, to contain biologically active (i.e., pesticidal) Cry toxins, researchers to date have not effectively utilized the protoxin forms of pesticidal polypeptides in conjunction with insect gut proteases to control plant pests. Moreover, these foreign proteins can be degraded and inactivated by proteases present in these transgenic plants. Thus, new strategies for modifying insect toxins and utilizing these modified insect toxins in pest management strategies are desired.

SUMMARY OF THE INVENTION

Compositions and methods for protecting a plant from an insect pest are provided. Compositions include nucleic acid molecules comprising nucleotide sequences encoding insect protoxins or insect toxins that comprise at least one proteolytic activation site that has been engineered to comprise a cleavage site that is sensitive to an insect gut protease. The proteolytic activation site is typically engineered within an activation region of the insect protoxin or insect toxin. Proteolytic cleavage of a modified insect protoxin by the insect gut protease releases the activated insect toxin within the insect gut. Cleavage of a modified insect toxin by the insect gut protease produces an active insect toxin with improved pesticidal activity in the insect gut relative to the corresponding insect toxin that lacks the proteolytic activation site. The nucleic acid molecules of the invention can be operably linked to any promoter of interest to drive expression of the modified insect protoxins or insect toxins in a plant or plant cell. Expression cassettes and transgenic plants, plant cells, and seeds comprising these novel nucleic acid molecules are also provided. Compositions comprising modified insect protoxins or modified insect toxins and methods of their use in controlling plant pests are further provided.

The nucleic acid compositions of the present invention find use in methods directed to protecting plants from insect pests. The methods comprise introducing into a plant a polynucleotide construct comprising a nucleotide sequence that encodes a modified insect protoxin operably linked to a promoter that drives expression in a plant. The modified insect protoxin comprises a proteolytic activation site that is engineered to comprise a cleavage site that is sensitive to an insect gut protease. Expression of the polynucleotide construct encoding the modified insect protoxin results in the production of the modified insect protoxin within the cells of the transgenic plant. When a susceptible insect pest feeds on the transgenic plant and, thus, also ingests the modified protoxin that has been expressed in the plant, the modified insect protoxin is cleaved by an insect gut protease to generate the active toxin in the insect gut, thereby impacting the insect pest.

Methods for protecting plants from an insect pest further comprise introducing into a plant a polynucleotide construct comprising a nucleotide sequence that encodes a modified insect toxin operably linked to a promoter that drives expression in a plant. The modified insect toxin comprises a proteolytic activation site that is engineered to comprise a cleavage site that is sensitive to an insect gut protease. Expression of the polynucleotide construct encoding the modified insect toxin results in the production of the modified insect toxin within the cells of the transgenic plant. When a susceptible insect pest feeds on the transgenic plant and, thus, also ingests the modified insect toxin that has been expressed in the plant, the modified insect toxin is cleaved by an insect gut protease to generate an active toxin in the insect gut that has improved pesticidal activity relative to the corresponding insect toxin that lacks the proteolytic activation site, thereby impacting the insect pest.

The present invention further provides nucleic acid molecules encoding insect gut proteases and biologically active variants and fragments thereof. The proteases are useful, for example, in methods directed to identification of preferred proteolytic cleavage sites for these insect gut proteases. Having identified these preferred proteolytic cleavage sites, insect protoxins and insect toxins of interest can be modified to comprise the preferred proteolytic cleavage sites within at least one proteolytic activation site to improve activation of the insect protoxin or toxin within an insect gut.

DETAILED DESCRIPTION OF THE INVENTION

The present invention is directed to compositions and methods that provide for protection of a plant from an insect pest, and which can be utilized to impact these insect pests. The compositions include novel nucleic acid molecules comprising nucleotide sequences encoding modified insect protoxins that provide for efficient processing into active toxins within the gut of the insect pest that feeds on a plant host expressing the modified insect protoxin. In some embodiments, the nucleic acid molecules of the invention comprise nucleotide sequences that encode modified insect protoxins that have at least one proteolytic activation site that has been engineered to comprise a cleavage site that is sensitive to an insect gut protease. Cleavage of a modified insect protoxin by an insect gut protease produces an active insect toxin in the insect gut. In other embodiments, the nucleic acid molecules of the invention comprise nucleotide sequences that encode modified insect toxins that have at least one proteolytic activation site that has been engineered to comprise a cleavage site that is sensitive to an insect gut protease. Cleavage of the modified insect toxin by an insect gut protease produces an insect toxin in the insect gut that displays improved pesticidal activity relative to the insect toxin that lacks the proteolytic activation site. The nucleic acids disclosed herein find use in methods for protecting a plant from an insect pest. "Modified insect protoxin" or "modified insect toxin" is intended to mean an insect protoxin or insect toxin that comprises at least one proteolytic activation site that is not naturally occurring within the insect protoxin or insect toxin, and which has been engineered to comprise a cleavage site that is sensitive to cleavage by an insect gut protease. "Sensitive to cleavage" is intended to mean that the protease recognizes the cleavage site, and thus is capable of cleaving the protoxin or toxin at that cleavage site. The non-naturally occurring proteolytic activation site is generally engineered within an activation region of the insect protoxin or insect toxin. "Activation region" in the context of an insect protoxin is intended to mean a region within the insect protoxin wherein proteolytic cleavage at the engineered activation site results in the production of a biologically active insect toxin. The "activation region" in the context of an insect toxin refers to a region within the insect toxin wherein proteolytic cleavage at the engineered activation site results in the production of an insect toxin with improved pesticidal activity, as defined herein. For purposes of the present invention, a biologically active insect toxin is also referred to as a "toxin," an "insect toxin," "active insect toxin," the "activated insect toxin," or the "activated form" of an insect protoxin.

The compositions of the invention also include polynucleotide constructs comprising these modified insect protoxin and insect toxin nucleic acid molecules. These constructs include, but are not limited to, expression cassettes, wherein the nucleotide sequences encoding the modified insect protoxins or modified insect toxins are operably linked to a promoter that drives expression in a plant cell. The invention further provides plant cells, plants, and seeds comprising a polynucleotide construct disclosed herein. The compositions of the invention are useful in protecting a plant from insect pests and can be utilized to impact insect pests that interact with a plant during one or more phases of the insect life cycle.

In some embodiments, the novel nucleic acid molecules of the invention comprise nucleotide sequences encoding a modified insect protoxin or insect toxin that comprises at least one proteolytic activation site that has been engineered to comprise a cleavage site that is sensitive to cleavage by a protease that resides within an insect gut. In particular embodiments, the proteolytic activation site is engineered to comprise a cleavage site that is the preferred cleavage site for a novel insect gut protease disclosed herein below.

The nucleic acid molecules encoding modified insect protoxins or modified insect toxins can be utilized in the methods of the invention to protect a plant from an insect pest. "Protecting a plant from an insect pest" is intended to mean limiting or eliminating insect pest-related damage to a plant by, for example, inhibiting the ability of the insect pest to grow, feed, and/or reproduce or by killing the insect pest. In some embodiments, a polynucleotide construct comprising a modified insect protoxin coding sequence, operably linked to a promoter that drives expression in a plant cell, can be introduced into a plant. Expression of this polynucleotide construct within cells of this plant produces the modified insect protoxin in those plant cells. When a susceptible insect pest feeds on cells of the plant that are expressing this modified insect protoxin, the ingested modified insect protoxin is cleaved by the insect gut protease, thereby producing an active insect toxin in the insect gut and impacting the insect pest. Similarly, when a polynucleotide construct comprising a nucleotide sequence encoding a modified insect toxin operably linked to a promoter that drives expression in a plant cell is introduced into a plant, the modified insect toxin is expressed. When an insect pest feeds on a plant expressing the modified insect toxin, the ingested modified insect toxin is cleaved by an insect gut protease, thereby producing an active insect toxin in the insect gut that displays improved pesticidal activity relative to the insect toxin lacking the engineered proteolytic activation site. The presence of the insect toxin with improved pesticidal activity in the insect gut impacts the insect pest.

In other embodiments, the invention is drawn to the modified insect protoxins and modified insect toxins encoded by the nucleic acid molecules of the present invention and to methods for using these polypeptides. Compositions and formulations comprising a modified insect protoxin or modified insect toxin, or variants or fragments thereof, that comprise at least one, non-naturally occurring proteolytic activation site that has been engineered to comprise a cleavage site that is sensitive to cleavage by an insect gut protease are further provided. The modified insect protoxin and modified insect toxin compositions of the invention are useful in methods directed to impacting insect pests. In this manner, the invention further provides a method for impacting an insect pest of a plant comprising applying, for example, a composition or formulation comprising a modified insect protoxin or modified insect toxin to the environment of the insect pest. As used herein, "impacting an insect pest of a plant" includes, but is not limited to, deterring the insect pest from feeding further on the plant, harming the insect pest by, for example, inhibiting the ability of the insect to grow, feed, and/or reproduce, or killing the insect pest. In one embodiment, the modified insect protoxin or modified insect toxin is combined with a carrier for subsequent application to the environment of the insect pest. While the invention is not bound by any theory of operation, in one embodiment, an insect pest ingests a modified insect protoxin composition. The modified insect protoxin is then cleaved by an insect gut protease to produce a biologically active toxin in the gut of the insect pest, thereby impacting the insect pest. Alternatively, an insect pest may ingest a modified insect toxin composition such that the insect toxin is then cleaved by an insect gut protease to produce an active insect toxin in the insect gut with improved activity relative to the insect toxin that lacks the proteolytic activation site. The presence of an insect toxin with improved pesticidal activity in the insect gut impacts the insect, as defined herein.

One of skill in the art would recognize that the compositions and methods of the invention can be used alone or in combination with other compositions and methods for controlling insect pests that impact plants. For example, the present invention may be used in conjunction with other pesticidal proteins or traditional chemical pesticides.

While the invention does not depend on a particular biological mechanism for protecting a plant from an insect pest, expression of the nucleotide sequences of the invention in a plant and ingestion of this plant by an insect pest can result in the production of active insect toxins, or active insect toxins with improved pesticidal activity, in the insect gut, resulting in increased resistance of the plant to insect pests. The transgenic plants of the invention find use in agriculture in methods for protecting plants from insect pests and for impacting insect pests. Certain embodiments of the invention provide transformed crop plants, such as, for example, maize plants, which find use in methods for impacting insect pests of the plant, such as, for example, western, northern, southern, and Mexican corn rootworms. Other embodiments of the invention provide transformed potato plants, which find use in methods for impacting the Colorado potato beetle, transformed cotton plants, which find use in methods for impacting the cotton boll weevil, and transformed turf grasses, which find use in methods for impacting the bluegrass billbug, *Sphenophorous parvulus*.

"Insect protoxin" or "protoxin" is intended to mean a biologically inactive polypeptide that is converted to an active insect toxin upon cleavage at a proteolytic activation site by a protease. In some embodiments, activation of the toxin proceeds by removal of a C-terminal peptide, an N-terminal peptide, or peptides from both the N-terminal and C-terminal regions of the protoxin. "Insect toxin" refers to a polypeptide the displays pesticidal activity, such as, for example, the activated form of an insect protoxin (i.e., the cleaved polypeptide that possesses pesticidal activity). Insect toxins of the invention include, for example, any polypeptide that displays pesticidal activity, such as, for example, *Bacillus thuringiensis* toxins, pentin-1, and variants and fragments thereof. As used herein, the term "pesticidal activity" refers to activity of a substance, such as, for example, a protein, that can be measured by routine assays known in the art. Such assays include, but are not limited to, pest mortality, pest weight loss, pest repellency, pest attraction, and other behavioral and physical changes of a pest after feeding and exposure to the substance for an appropriate length of time. General procedures include addition of the experimental compound or organism to the diet source in an enclosed container. Assays for assessing pesticidal activity are well known in the art. See, e.g., U.S. Pat. Nos. 6,570,005 and 6,339,144; herein incorporated by reference in their entirety.

In some embodiments, a modified insect toxin is cleaved by an insect gut protease to produce an insect toxin with improved pesticidal activity relative to the corresponding insect toxin that lacks the proteolytic activation site. As used herein the term "improved pesticidal activity" characterizes an insect toxin of the invention that has enhanced pesticidal activity relative to the activity of the corresponding unmodified insect toxin (i.e., the insect toxin that lacks the engineered proteolytic activation site). Improved pesticidal activity refers to any increase in the pesticidal activity of the cleaved insect toxin when compared with the pesticidal activity of the insect toxin lacking the proteolytic activation site. In some embodiments, a finding of improved or enhanced pesticidal activity requires a demonstration of an increase of toxicity of at least 10%, against the insect target, and more preferably 20%, 25%, 30%, 35%, 40%, 45%, 50%, 60%, 70%, 100%, 200%, or greater increase of toxicity relative to the pesticidal activity of the insect toxin lacking the engineered proteolytic activation site, as determined against the same insect. Any standard assay for measuring pesticidal activity can also be used to assess increases in pesticidal activity.

The preferred developmental stage for testing for pesticidal activity is larvae or immature forms of an insect of interest. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

In some embodiments of the invention, the insect toxin is a *Bacillus thuringiensis* (Bt) toxin. "Bt" or "*Bacillus thuringiensis*" toxin is intended to mean the broader class of toxins found in various strains of *Bacillus thuringiensis*, which includes such toxins as, for example, the vegetative insecticidal proteins and the δ-endotoxins. See, for example, Crickmore et al. (2004) *Bacillus Thuringiensis Toxin Nomenclature* at lifesci.sussex.ac.uk/Home/Neil_Crickmore/Bt and Crickmore et al. (1998) *Microbiol. Molec. Biol. Rev.* 62:807-813, both of which are herein incorporated by reference in their entirety. The vegetative insecticidal proteins (for example, members of the VIP1, VIP2, or VIP3 classes) are secreted insecticidal proteins that undergo proteolytic processing by midgut insect fluids. They have pesticidal activity against a broad spectrum of Lepidopteran insects. See, for example, U.S. Pat. No. 5,877,012, herein incorporated by reference in its entirety. The Bt δ-endotoxins are toxic to larvae of a number of insect pests, including members of the Lepidoptera, Diptera, and Coleoptra orders. These insect protoxins include, but are not limited to, the Cry toxins, including, for example, Cry1, Cry 2, Cry3, Cry4, Cry5, Cry6, Cry7, Cry8, and Cry9. Of particular interest are the Cry8-like δ-endotoxins. "Cry8-like" toxins include the nucleotide or amino acid sequence that share a high degree of sequence identity or similarity to previously described sequences categorized as Cry8, which includes such toxins as, for example, Cry8Bb1 (see Genbank Accession No. CAD57542; SEQ ID NO:10 (nucleotide sequence); SEQ ID NO:11 (amino acid sequence)) and Cry8Bc1 (see Genbank Accession No. CAD57543; SEQ ID NO:12 (nucleotide sequence); SEQ ID NO:13 (amino acid sequence)). See copending U.S. patent application Ser. No. 10/606,320, entitled, "Genes Encoding Proteins with Pesticidal Activity," filed Jun. 25, 2003, herein incorporated by reference. "Cry8-like insect protoxin" is intended to mean the biologically inactive polypeptide that is converted to the activated Cry8-like insect toxin upon cleavage at a proteolytic activation site by a protease. It is the activated Cry8-like insect toxin that has pesticidal activity. As used herein, "Cry8-like insect toxin" refers to a biologically active pesticidal polypeptide that shares a high degree of sequence identity or similarity to Cry8 insect toxin sequences.

The Bt toxins are a family of insecticidal proteins that are synthesized as protoxins and crystallize as parasporal inclusions. When ingested by an insect pest, the microcrystal structure is dissolved by the alkaline pH of the insect midgut, and the protoxin is cleaved by insect gut proteases to generate the active toxin. The activated Bt toxin binds to receptors in the gut epithelium of the insect, causing membrane lesions and associated swelling and lysis of the insect gut. Insect death results from starvation and septicemia. See, e.g., Li et al. (1991) *Nature* 353:815-821.

The protoxin form of the Cry toxins contains a crystalline forming segment. A comparison of the amino acid sequences of active Cry toxins of different specificities further reveals five highly conserved sequence blocks. Structurally, the Cry toxins comprise three distinct domains, which are, from the N- to C-terminus: a cluster of seven alpha-helices implicated in pore formation (referred to as "domain 1"), three antiparallel beta sheets implicated in cell binding (referred to as "domain 2"), and a beta sandwich (referred to as "domain 3"). The location and properties of these domains are known to those of skill in the art. See, for example, Li et al. (1991) supra and Morse et al. (2001) *Structure* 9:409-417.

Other examples of insect toxins include, for example, pentin-1 and pentin-like proteins (see U.S. Pat. Nos. 6,057,491 and 6,339,144, both of which are herein incorporated by reference in their entirety). "Pentin-1 like" is intended to mean that the nucleotide or amino acid sequence shares a high degree of sequence identity or similarity to previously described pentin-1 sequences.

The modified insect protoxins or modified insect toxins of the invention can be derived from any suitable native (i.e., naturally occurring) insect protoxin or insect toxin, such as the native Bt δ-endotoxins described above, by engineering the proteolytic activation site of interest within the native insect protoxin or insect toxin sequence. In this manner, a nucleotide sequence encoding the native insect protoxin or insect toxin of interest can be altered, for example, by site-directed mutagenesis, to comprise the codons for the proteolytic activation site of interest, i.e., a site sensitive to insect gut proteases. As noted above, the codons for the proteolytic activation site(s) of interest are engineered within the region of the native coding sequence that corresponds to an activation region of the native insect protoxin or insect toxin, so that proteolytic cleavage of the encoded modified insect protoxin or modified insect toxin by the protease of interest results in production of the active insect toxin or an active insect toxin with improved pesticidal activity.

Alternatively, the modified insect protoxins or modified insect toxins of the invention can be derived from fragments or variants of native insect protoxins or native insect toxins, as defined herein below, so long as the fragment or variant of the native insect protoxin or insect toxin yields an activated (i.e., having pesticidal activity) insect toxin, or a toxin having improved pesticidal activity in the case of a modified insect toxin, upon proteolytic cleavage by the insect gut protease of interest. In this manner, the coding sequences for such fragments and variants of the native insect protoxin or insect toxin protein serve as the starting material for engineering in the codons for the proteolytic activation site(s) of interest. In essence, a modified insect protoxin or modified insect toxin designed in this manner represents a fragment or variant of the native insect protoxin or insect toxin that has been engineered to comprise the proteolytic activation site of interest within an activation region of the respective polypeptide. Examples of variants and fragments of insect protoxins and toxins are provided in copending U.S. patent application Ser. No. 10/606,320, entitled "Genes Encoding Proteins with Pesticidal Activity," filed Jun. 25, 2003 and U.S. patent application Ser. No. 10/746,914, entitled "Genes Encoding Proteins with Pesticidal Activity," filed Dec. 24, 2003, both of which are herein incorporated by reference in their entirety.

It is recognized that variations in a modified insect protoxin or modified insect toxin disclosed herein can be introduced at the level of the nucleic acid molecule that encodes a modified form of a native insect protoxin or insect toxin in order to produce a variant of the encoded modified insect protoxin or modified insect toxin. That is, having disclosed a nucleotide sequence encoding a native insect protoxin or insect toxin with at least one proteolytic activation site of interest engineered within the native sequence, one of skill in the art can subsequently introduce variations into the disclosed nucleotide sequence of the invention, so that the encoded modified insect protoxin or modified insect toxin is a variant of the modified native insect protoxin or modified native insect toxin. Such variations include deletions, substitutions, and additions of one or more residues, and include variations that result in truncated forms of the modified insect protoxin. Any such variations can be introduced into the nucleotide sequence encoding the modified native insect protoxin or modified insect toxin so long as the encoded variant of the modified native insect protoxin or modified insect toxin can be cleaved to produce a biologically active insect toxin, i.e., an insect toxin that has pesticidal activity as noted elsewhere herein, or, in the case of a modified insect toxin, a toxin with improved pesticidal activity relative to the insect toxin that lacks the proteolytic activation site. Such variants and fragments are well-known in the art. See, e.g., copending U.S. patent application Ser. No. 10/606,320, filed Jun. 25, 2003; and U.S. Pat. No. 5,877,012; herein incorporated by reference in their entirety.

A "protease" is intended to mean an enzyme that cleaves polypeptides by hydrolyzing peptide bonds. As used herein, "insect gut protease" refers to a protease that is naturally found in the digestive tract of an insect pest. Researchers have established that a wide array of proteases is expressed in the insect gut, including cysteine and serine proteases. See, e.g., Shiba et al. (2001) *Arch. Biochem. Biophys.* 390:28-34; see also, Purcell et al. (1992) *Insect Biochem. Mol. Biol.* 22:1-47; Koiwa et al. (2000) *FEBS Letters* 471:67-70; Koiwa et al. (2000) *Anal. Biochem.* 282:153-155. Any insect gut protease may be used in the present invention. In some embodiments, the insect gut protease is a cysteine protease, for example, a cathepsin L-like protease. In particular embodiments, the insect gut protease is a cathepsin L-like protease disclosed herein below.

A "proteolytic site" is intended to mean an amino acid sequence that confers sensitivity to a class of proteases or a particular protease such that a polypeptide comprising the amino acid sequence is cleaved at that site by members of the class of proteases or by the particular protease. As used herein, a "proteolytic activation site" is a proteolytic site that has been engineered into an activation region of an insect protoxin or an insect toxin. As used herein in the context of an insect protoxin, an "activation region" is a region of an insect protoxin such that proteolytic cleavage at the proteolytic activation site within the activation region generates a biologically active insect toxin. An "activation region" in an insect toxin refers to a region of an insect toxin such that proteolytic cleavage at the proteolytic activation site within the activation region generates an insect toxin that displays improved pesticidal activity relative to the corresponding insect toxin lacking the engineered proteolytic activation site. A proteolytic site is said to be "sensitive" to the protease(s) that recognizes that site. It is recognized that the efficiency of proteolytic digestion will vary, and that a decrease in efficiency of proteolytic digestion can lead to an increase in stability or longevity of the polypeptide within a plant cell or within an insect gut. Thus, a proteolytic site may confer sensitivity to more than one protease or class of proteases, but the efficiency of digestion at that site by various proteases may vary.

Proteolytic sites include, for example, trypsin sites, chymotrypsin sites, papain sites, cathepsin sites, and cathepsin-like sites. Proteolytic sites for particular proteases often comprise "motifs," or sequence patterns, that are known to confer sensitivity to a particular protease. Thus, for example, cathepsin site motifs include FRR, a cathepsin L protease cleavage site; RR, a trypsin and cathepsin B cleavage site; LKM, a chymotrypsin site; and FF, a cathepsin D site. A putative proteolytic site is a sequence that comprises a motif or comprises a sequence similar to a motif but which has not been shown to be subject to digestion by the corresponding protease. In one embodiment, the modified insect protoxins or modified insect toxins of the invention have a proteolytic activation site that comprises the motif LXQS (SEQ ID NO:1), more particularly, LSQS (SEQ ID NO:2). In other embodiments, the proteolytic activation site comprises LXQSLXQS (SEQ ID NO:3), more particularly LSQSLSQS (SEQ ID NO:4).

The engineered proteolytic activation site may replace a naturally occurring site within the insect protoxin or insect toxin. For example, in one embodiment, the NGSR (SEQ ID NO:5) sequence located between the loop of alpha helices 3 and 4 in domain I of the Cry8 insect protoxin is replaced with LSQS (SEQ ID NO:2) or LSQSLSQS (SEQ ID NO:4). In other embodiments of the invention, the proteolytic activation site is introduced in the C-terminal portion of the protoxin, the N-terminal portion of the protoxin, or in both the N terminal and C-terminal regions. Likewise, in some embodiments, cleavage of the protoxin will result in the removal of an N-terminal peptide, a C-terminal peptide, or peptides from both the N-terminal and C-terminal regions of the protein. In one particular embodiment, the proteolytic activation site is introduced in the junction between the N-terminal crystalline forming segment of the protoxin and the C-terminal portion of the protoxin that comprises the active insect toxin upon cleavage.

It is further recognized that insect protoxins or insect toxins expressed in a plant may be susceptible to further cleavage by plant proteases. A "plant protease" is intended to mean a protease that is naturally found in any plant of the invention. Previous research has shown that plants express a variety of proteases, including serine and cysteine proteases. See, e.g., Goodfellow et al. (1993) *Plant Physiol.* 101:415-419; Pechan et al. (1999) *Plant Mol. Biol.* 40:111-119; Lid et al. (2002) *Proc. Nat. Acad. Sci. USA* 99:5460-5465. In some embodiments, the plant protease is a cysteine protease, for example, a cathepsin or cathepsin-like protease. In one embodiment, the cysteine protease is a cathepsin B-like protease. Cleavage of the insect protoxin or insect toxin by a plant protease at a naturally occurring proteolytic site may lead to, for example, premature processing, degradation, or activation of the protoxin or toxin in the plant, rather than in the insect gut where it will be most effective. In particular embodiments, incorporation of a proteolytic activation site that has been engineered to comprise a cleavage site that is sensitive to an insect gut protease also stabilizes the insect protoxin or toxin in the plant. As used herein, "stabilizes the insect toxin in the plant" means that incorporation of the engineered proteolytic activation site protects the insect protoxin or insect toxin from, for example, premature processing, degradation (complete or partial), or activation in the plant. Cleavage of the insect protoxin or insect toxin at a naturally occurring proteolytic site by a plant protease may also lead to proteolytic inactivation of the toxin. As used herein, "proteolytic inactivation" connotes cleavage of the insect protoxin or insect toxin at a naturally occurring proteolytic site by a plant protease, wherein cleavage at that site reduces or eliminates the pesticidal activity of the resulting insect toxin. In one embodiment, the insect protoxin or insect toxin is engineered to replace a naturally occurring proteolytic site that is sensitive to cleavage by a plant protease with a proteolytic protection site. A "proteolytic protection site" is intended to mean a site that is not sensitive to cleavage by an endogenous plant protease. Replacement of a naturally occurring proteolytic site sensitive to cleavage by a plant protease with a proteolytic protection site protects the insect protoxin or insect toxin from proteolytic inactivation by the plant. See, for example, copending U.S. patent application Ser. No. 10/746,914, entitled "Genes Encoding Proteins with Pesticidal Activity," filed Dec. 24, 2003, herein incorporated by reference in its entirety. Protection of an insect protoxin or an insect toxin from premature processing, degradation, or inactivation by any plant protease is encompassed by the present invention.

In some embodiments, an insect protoxin or insect toxin is engineered to comprise a proteolytic activation site that is recognized by an insect gut protease. The invention provides nucleic acid molecules, and variants and fragments thereof, that encode insect gut proteases. Specifically, the invention provides nucleic acid molecules encoding proteases identified in the midgut of *Diabrotica virgifera virgifera* (i.e., western corn rootworm, hereinafter WCRW). The nucleotide sequences set forth in SEQ ID NOs:6 and 8 encode cysteine proteases that belong to the cathepsin L-like subfamily of proteases. The nucleotide sequences set forth in SEQ ID NOs:6 and 8 encode the polypeptide sequences (i.e., proteases) of SEQ ID NOs:7 and 9, respectively. The protease comprising the amino acid sequence of SEQ ID NO:7 is 100% identical to a protease recently isolated from corn rootworm. See Brown et al. (2004) *Insect Biochem. Mol. Biol.* 34:305-320. The protease comprising the amino acid sequence of SEQ ID NO:9 is 79% identical to another protease isolated by Brown et al. The invention further encompasses variants and fragments of these polypeptide sequences that possess proteolytic activity as defined herein below. Assays for measuring proteolytic activity are well known in the art.

Studies indicate that the cathepsin L-like proteases of the invention represent the two most abundant forms of the cathepsin-type proteases expressed within the WCRW midgut and, therefore, are expected to be significantly involved in the digestive process. See Example 1. Previous research has demonstrated that mammalian cathepsin L-like proteases have a general preference for F-R-(A/S/K/N/Q) with cleavage C-terminal to the arginine position. Little is known about the proteolytic cleavage site(s) for insect pest cathepsin L-like proteases. Thus, the WCRW gut proteases of the invention find use, for example, in identifying the preferred proteolytic cleavage site(s) for these proteases. In another embodiment, the insect gut proteases are used to identify proteolytic cleavage sites within pesticidal polypeptides, for example, Cry8-like toxins such as Cry8Bb1 and Cry8Bc1, that are susceptible to these proteases.

Knowledge about the preferred proteolytic sites for the insect gut proteases of the invention may lead to improvements in the activation and stability of insect toxins. For example, a proteolytic activation site that is sensitive to cleavage by an insect gut protease of the invention may be introduced into an activation region of an insect protoxin or insect toxin. When this modified insect protoxin or insect toxin is expressed in a plant and an insect pest, such as WCRW, feeds on the transgenic plant, the protoxin or toxin is cleaved by a cathepsin L-like protease of the invention in the gut of the insect, thereby producing the active toxin or an insect toxin with improved pesticidal activity and impacting the insect pest. In one embodiment, the engineered proteolytic activation site is sensitive to cleavage by the cathepsin L-like protease of SEQ ID NO:7 or 9. In some embodiments, the insect protoxin is a Cry8-like protoxin.

It is further recognized that insect protoxins or toxins expressed in a plant may be susceptible to cleavage by insect gut proteases upon ingestion by an insect pest. Cleavage of an active insect toxin by an insect gut protease may lead to proteolytic inactivation of the toxin. In this context, "proteolytic inactivation" refers to cleavage of an insect protoxin or insect toxin at a proteolytic site by an insect gut protease, wherein cleavage at that site reduces or eliminates the pesticidal activity of the resulting toxin. In one embodiment, an insect protoxin or toxin is engineered to replace a proteolytic site that is sensitive to cleavage by an insect gut protease with a proteolytic protection site. In this context, "proteolytic protection site," refers to a site that is not sensitive to cleavage by an insect gut protease. Replacement of a proteolytic site sensitive to cleavage by an insect gut protease with a proteolytic protection site protects the insect protoxin or insect toxin from proteolytic inactivation in the insect gut. Eliminating protease-sensitive sites may prevent the insect protoxin or insect toxin from rapid degradation in the insect midgut after ingestion, allowing the toxin to reach its target intact and more rapidly reach an insecticidal dose within the insect pest. In one embodiment, the proteolytic protection site is engineered to be insensitive to cleavage by a cathepsin L-like protease of the invention, i.e., the polypeptide of SEQ ID NO:7 or 9.

The nucleic acids of the invention encoding cathepsin L-like insect gut proteases (SEQ ID NOs:6 and 8) and the polypeptides they encode (SEQ ID NOs:7 and 9) find further use in identifying and designing inhibitors of these proteases. Chemical and biological agents that inhibit these proteases could exhibit strong pesticidal effects upon insect feeding. For example, such inhibitors may result in the inability of the insect pest to digest food and supply the necessary dietary factors needed to support growth and development. In some embodiments, the inhibitors of the cathepsin L-like proteases of the invention are polypeptides. In a particular embodiment, nucleic acid molecules encoding the polypeptide inhibitors of the insect gut proteases of the invention are used to generate transgenic plants. These plants find use in controlling an insect pest of a plant. In other embodiments, polypeptide inhibitors of the cathepsin L-like proteases of the invention are used to control pests by applying the inhibitor composition to the environment of pests.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the terms "polynucleotide constructs" or "nucleotide constructs" herein is not intended to limit the present invention to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the invention additionally encompass all complementary forms of such constructs, molecules, and sequences. Further, the nucleotide constructs, nucleotide molecules, and nucleotide sequences of the present invention encompass all nucleotide constructs, molecules, and sequences that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the invention also encompass all forms of nucleotide constructs including, but not limited to, single-stranded forms, double-stranded forms, hairpins, stem-and-loop structures, and the like.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, the term "recombinantly engineered" or "engineered" or "modified" connotes the utilization of recombinant DNA technology to introduce (e.g., engineer) a change in the protein structure based on an understanding of the protein's mechanism of action and a consideration of the amino acids being introduced, deleted, or substituted. For example, a nucleic acid molecule encoding an insect protoxin may be engineered to comprise a coding sequence for a proteolytic activation site as described elsewhere herein.

As used herein, "full-length sequence" in reference to a specified polynucleotide or its encoded protein means having the entire nucleic acid sequence or the entire amino acid sequence of a native sequence. By "native sequence" is intended an endogenous sequence, i.e., a non-engineered sequence found in an organism's genome. A full-length polynucleotide encodes the full-length form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein. Hence, fragments of an insect protoxin nucleotide sequence may encode protein fragments that become active insect toxins (i.e., possess pesticidal activity) upon cleavage by a protease. Fragments of an insect toxin may encode protein fragments that become insect toxins with improved pesticidal activity upon cleavage by an insect gut protease. In contrast, fragments of an insect gut protease nucleotide sequence of the invention may encode protein fragments that have proteolytic activity as described herein and recognize the preferred proteolytic cleavage site of the native protease. Alternatively, fragments of a polynucleotide that are useful as hybridization probes generally do not encode fragment proteins that retain biological activity. Thus, fragments of a nucleotide sequence may range from at least about 20 nucleotides, about 50 nucleotides, about 100 nucleotides, and up to the full-length polynucleotide encoding the polypeptides of the invention.

A fragment of a polynucleotide of the invention that encodes a biologically active portion of a protein of the invention will encode at least 15, 25, 30, 50, 100, 150, 200, or 250 contiguous amino acids, or up to the total number of amino acids present in a full-length protein of the invention. Fragments of a nucleotide sequence that are useful as hybridization probes or PCR primers generally need not encode a biologically active portion of a protein of the invention.

Thus, a fragment of a polynucleotide disclosed herein may encode a biologically active portion of an insect protoxin, an insect toxin, or an insect gut protease, or it may be a fragment that can be used as a hybridization probe or PCR primer using methods disclosed below. A biologically active portion of an insect gut protease can be prepared by isolating a portion of one of the insect gut protease polynucleotides of the invention, expressing the encoded portion of the protease (e.g., by recombinant expression in vitro), and assessing the activity of the encoded portion of the insect gut protease. Polynucleotides that are fragments of a nucleotide sequence of the invention comprise at least 16, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length polynucleotide disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the insect protoxins or insect gut proteases. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:9 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, for example, protease activity as described herein. Such variants may result from, for example, genetic polymorphism or from human manipulation. Biologically active variants of a native insect protoxin or insect gut protease of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the protoxin or protease proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of an insect protoxin or toxin can be evaluated by, for example, insect-feeding assays. See, e.g., Marrone et al. (1985) *J. Econ. Entomol.* 78:290-293 and Czapla and Lang (1990) supra, herein incorporated by reference. Assays for assessing the proteolytic activity of an insect gut protease of the invention are well known in the art.

Variant polynucleotides and proteins also encompass sequences and proteins derived from a mutagenic and recombinogenic procedure such as DNA shuffling. With such a procedure, one or more different coding sequences can be manipulated to create a new protoxin, toxin, or protease protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the gene of the invention and other known genes to obtain a new gene coding for a protein with an improved property of interest, such as an increased $K_m$ in the case of an insect gut protease. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants or insects. In this manner, methods such as PCR, hybridization, and the like can be used to identify such sequences based on their sequence homology to the sequences set forth herein. Sequences isolated based on their sequence identity to the entire insect protoxin. toxin, or insect gut protease sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode an insect protoxin, insect toxin, or an insect gut protease and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire insect gut protease polynucleotide disclosed herein, or one or more portions thereof, may be used as a probe capable of specifically hybridizing to corresponding insect gut protease polynucleotides and messenger RNAs. To achieve specific hybridization under a variety of conditions, such probes include sequences that are unique among insect gut protease polynucleotide sequences and are optimally at least about 10 nucleotides in length, and most optimally at least about 20 nucleotides in length. Such probes may be used to amplify corresponding insect gut protease polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning. A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The insect protoxin, insect toxin, and insect gut protease polynucleotide sequences of the invention can be provided in expression cassettes for expression in the plant of interest. The cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the insect protoxin or insect gut protease polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a polynucleotide of the invention, and a transcriptional and translational termination region (i.e., termination region) functional in plants. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence. While it may be optimal to express the sequences using heterologous promoters, the native promoter sequences may be used.

The termination region may be native with the transcriptional initiation region, may be native with the operably linked polynucleotide of interest, may be native with the plant host, or may be derived from another source (i.e., foreign or heterologous to the promoter, the polynucleotide of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J. Cell Science* 117:943-54 and Kato et al. (2002) *Plant Physiol* 129:913-42), and yellow fluorescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol. 78* (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced modified insect protoxin expression within a particular plant tissue. Tissue-preferred promoters include Yamamoto et al. (1997) *Plant J* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

In particular embodiments, modified insect protoxins or modified insect toxins are selectively expressed in plant roots where insect-related damage is likely to occur. Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed ro1C and ro1D root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. Other root-preferred promoters of interest are disclosed in U.S. patent application Ser. No. 11/022,111, entitled "Maize Metallothionein Promoter," filed Dec. 22, 2004, and U.S. patent application Ser. No. 11/022,449, entitled "Maize Metallothionein 2 *Promoter and Methods of Use," filed Dec.* 22, 2004, both of which are herein incorporated by reference in their entirety.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. Nos. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the insect protoxin or insect toxin sequences of the invention can be provided to a plant using a variety of transient transformation methods. Such transient transformation methods include, but are not limited to, the introduction of the insect protoxin or insect toxin protein, or variants and fragments thereof, directly into the plant or the introduction of the a protein transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci. USA* 91:2176-2180 and Hush et al. (1994) *J. Cell Science* 107:775-784, all of which are herein incorporated by reference. Alternatively, the insect protoxin or insect toxin polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the a modified insect protoxin or modified insect toxin of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5; etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., expression of a modified insect protoxin or modified insect toxin), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in Fehr (1993) *Principals of Cultivar Development* (Macmillan Publishing Company) the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The invention also encompasses transformed or transgenic plants comprising at least one nucleotide sequence of the invention. Optimally, the plant is stably transformed with a nucleotide construct comprising at least one nucleotide sequence of the invention operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The present invention may be used for transformation and protection of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Compositions comprising an isolated insect protoxin or an isolated insect toxin that has at least one proteolytic activation site that has been engineered to comprise a cleavage site that is sensitive to an insect gut protease are further provided. In the present invention, an isolated modified insect protoxin protein or modified insect toxin can be formulated with an acceptable carrier into a protoxin or toxin composition or formulation that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the modified protoxin or toxin proteins of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluant before application. The modified insect protoxin or modified insect toxin concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb.-5.0 lb. per acre when in dry form and at about 0.01 pts.-10 pts. per acre when in liquid form.

In a further embodiment, the compositions of the invention can be treated prior to formulation to prolong the pesticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The modified protoxin and modified toxin compositions and formulations of the invention can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, a modified insect protoxin or modified insect toxin protein of the invention may be mixed with grain to protect the grain during storage. It is generally important to obtain good control of pests in the early stages of plant growth, as this is the time when the plant can be most severely damaged. The compositions of the invention can conveniently contain another insecticide if this is thought necessary. In an embodiment of the invention, the composition is applied directly to the soil, at a time of planting, in granular form of a composition of a carrier. Another embodiment is a granular form of a composition comprising an agrochemical such as, for example, a herbicide, an insecticide, a fertilizer, or an inert carrier.

Compositions of the invention find use in protecting plants, seeds, and plant products in a variety of ways. For example, the compositions can be used in a method that involves placing an effective amount of the modified insect protoxin or modified insect toxin composition in the environment of the pest by a procedure selected from the group consisting of spraying, dusting, broadcasting, or seed coating. While not intending to be limited to a particular mechanism, in one embodiment an insect pest ingests a modified insect protoxin composition, and the insect protoxin is then cleaved by a protease present in the insect gut. Cleavage of the insect protoxin produces an active insect toxin in the insect gut, which in turn impacts the insect pest. In other embodiments, a modified insect toxin composition is applied to the environment of an insect pest and is subsequently ingested by an insect pest. The modified insect toxin is then cleaved by an insect gut protease to produce an active insect toxin in the insect gut that displays improved pesticidal activity relative to the corresponding insect toxin that lacks the engineered proteolytic activation site.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding a modified protoxin or modified toxin protein of the invention may be treated with a seed protectant coating comprising a seed treatment compound, such as, for example, captan, carboxin, thiram, methalaxyl, pirimiphos-methyl, and others that are commonly used in seed treatment. In one embodiment within the scope of the invention, a seed protectant coating comprising a pesticidal composition of the invention is used alone or in combination with one of the seed protectant coatings customarily used in seed treatment.

The methods and compositions of the present invention may be effective against a variety of pests. For purposes of the present invention, pests include, but are not limited to, insects, fungi, bacteria, nematodes, acarids, protozoan pathogens, animal-parasitic liver flukes, and the like. Pests of particular interest are insect pests, particularly insect pests that cause significant damage to agricultural plants.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; Siphaflava, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, two spotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabari-* nus, carmine spider mite; *Tetranychus urticae*, two spotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis*; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis*/psilon, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The article "a" and "an" are used herein to refer to one or more than one (i.e., to at least one) of the grammatical object of the article. By way of example, "an element" means one or more element.

The following examples are presented by way of illustration, not by way of limitation.

EXPERIMENTAL

Example 1

Preparation and Sequencing of cDNA Libraries from Western Corn Rootworm Midguts

Midguts from 50 3$^{rd}$ instar western corn rootworm (WCRW) (*Diabrotica virgifera virgifera*) were dissected and harvested directly into liquid nitrogen. Total RNA was prepared by tissue homogenization in liquid nitrogen using a mortar and pestle followed by cell lysis in the presence of TRIzol (Invitrogen, Carlsbad, Calif.).

For cDNA library construction, polyA(+) RNA was purified from the total RNA on an oligo(dT)-cellulose affinity column using the mRNA Purification Kit (Amersham Pharmacia Biotech, Piscataway, N.J.), according to the kit's protocol. The first strand cDNA synthesis using Superscript II (Invitrogen) and subsequent second strand synthesis, linker addition, and directional cloning into the EcoRI and XhoI sites of pBlueScript SK+ (Stratagene, La Jolla, Calif.) were performed in accordance with the instructions provided with the Stratagene cDNA kit (Stratagene). cDNA was purified using a cDNA column (Invitrogen) immediately prior to ligation into the vector.

Sequencing of cDNA library clones was accomplished using the ABI PRISM Big Dye Terminator Cycle Sequencing Ready reaction kit with FS AmpliTaq DNA polymerase (Perkin Elmer, Boston, Mass.) and analyzed on an ABI Model 373 Automated DNA Sequencer.

Sequences resulting from approximately 7000 clones were compared to known nucleotide or peptide sequences in GenBank and Peptide Sequence databases using BLASTN or BLASTP programs.

Sequence analysis of these ESTs indicated that the predominant midgut proteases in WCRW were cysteine proteases belonging to the cathepsin family (Table 1). In terms of relative abundance, cathepsin L was the major cathepsin protease followed by cathepsin B and cathepsin D. Cathepsin L members accounted for over 83% of the cathepsin sequences found in the sequenced clones. Cluster analysis revealed that two members from this family, iwm2s.pk017.h10 (hereinafter "h10"; SEQ ID NO:6 (nucleotide sequence); SEQ ID NO:7 (amino acid sequence)) and iwm2s.pk015.c9 (hereinafter "c9"; SEQ ID NO:8 (nucleotide sequence); SEQ ID NO:9 (amino acid sequence), together make up 80% of the cathepsin L sequences and 46% of all of the cathepsin sequences found in the library sequence. Trypsin was also identified from the midgut sequences but represented less than 2% of midgut proteases.

TABLE 1

Distribution of proteases in WCR midgut ESTs

| Protease | % of protease represented in cDNA library |
|---|---|
| Cathepsin L | 82.1 |
| Cathepsin B | 10.6 |
| Cathepsin D | 4.5 |
| Trypsin | 1.9 |
| Chymotrypsin | 0 |

Example 2

Recombinant Expression of h10 (SEQ ID NO:7 and c9 (SEQ ID NO:9) proteases

The two most abundant cathepsins, represented by h10 (SEQ ID NO:7) and c9 (SEQ ID NO:9), were fully sequenced to obtain full-length genes. The predicted amino acid sequence indicated that these proteins were 315 and 314 amino acids in length, respectively. h10 is 100% identical to a cysteine protease recently isolated from CRW (Brown et al. (2004) *Insect Biochem. Mol. Biol.* 34(4):305-320), and c9 is 79% identical to another CRW cysteine protease isolated by Brown et al. As expected, h10 and c9 contain a signal peptide and a propeptide region immediately upstream of the mature protease.

In order to characterize the cleavage sites recognized by the two cathepsin L-like proteases, both c9 and h10 were expressed using the EasySelect™ *Pichia* Expression Kit (Invitrogen). The coding sequences of h10 and c9 were PCR amplified with platinum high fidelity polymerase (Invitrogen, Carlsbad, Calif.) using primers:

```
                                                  (SEQ ID NO:14)
h10 fwd: CGACTCGAGAAAAGAAATCTAGGTGCCTTCGAAAAATGG (SEQ ID NO:15)
h10 rev: CCATTATATGCGGCCGCCTACAATTTAGGGTAAGAGTTCATG (SEQ ID NO:16)
c9  fwd: CGACTCGAGAAAGAAATTTATCTGCCTTTGAGCAATGG (SEQ ID NO:17)
c9  rev: CCTATATTAGCGGCCGCCTACAACTTGGGGTAAGAGTTC
```

The forward (fwd) primers were designed to correspond to sequence encoding the beginning of the predicted propeptide region and included a partial α mating factor signal sequence and a Kex2 cleavage site upstream of propeptide sequence. This combination would ensure that once cloned into the Pichia expression vector pPICZαA (Invitrogen) the complete a mating factor signal sequence would be reconstituted and recombinant cathepsin would be secreted into the growth medium and then subsequently removed by the Kex2 protease. Additional restriction sites for XhoI and NotI were included in the fwd and rev primers (underlined in the above sequences) to facilitate subsequent cloning steps. The amplified fragments were digested with XhoI and NotI and cloned in pBluescript SK (Stratagene, La Jolla, Calif.) for sequence confirmation before subcloning into the same restriction sites in pPICZαA for expression.

The resulting plasmids, pPICZα-c9 and pPICZα-h10, were transformed into chemically competent X-33 Pichia pastoris cells using the Pichia EasyComp™ Transformation kit (Invitrogen) following the kit's instructions. Transformants were selected on Zeocin™ (100 µg/ml) containing YPDS agar plates (1% yeast extract, 2% peptone, 2% dextrose, 1 M sorbitol, 2% agar). Small-scale expression testing of 5 to 10 Zeocin™-resistant transformants was performed to evaluate recombinant c9 and h10 cathepsin production. Individual transformants were inoculated and grown overnight at 30° C. in 25 ml BMGY media (1% yeast extract, 2% peptone, 100 mM potassium phosphate pH 6, 1.34% yeast nitrogen base (YNB), 4×10$^{-5}$% Biotin, 1% glycerol). Expression was induced by harvesting cells by centrifugation at 3000×g for 5 minutes at room temperature, decanting the supernatant and resuspending the cell pellet in BMMY media (BMGY−1% glycerol+0.5% methanol) to an $OD_{600}$ of 1.0. The resulting cultures were incubated at 30° C. in a shaking incubator. Induction was maintained over a 96 hr period by addition of 100% methanol to a 0.5% final concentration every 24 h.

The supernatant from each culture was collected by pelleting the cells and transferring the supernatant to a new tube and storing at −80° C. c9 and h10 protein expression was analyzed by Coomasie-stained SDS-PAGE. SDS-PAGE indicated that c9 and h10 were being expressed and secreted into the culture media in its propeptide form based on their predicted molecular weight sizes of 33 kDa. N-terminal amino acid sequence analysis confirmed that the 33 kDa bands corresponded to the propeptides. Reducing the pH from neutral to acidic (pH 4.5) resulted in autoprocessing of the propeptide into its mature 22 kDa form, demonstrating that c9 and h10 were functionally expressed by Pichia pastoris. N-terminal amino acid sequence analysis confirmed that the 22 kDa band represented the mature form. Some differential autoprocessing between the pro- and mature peptide was observed by the sequence analysis.

Example 3

Functional Characterization of c9 and h10 Cathepsins on Synthetic Peptide Substrates Further functional characterization of c9 and h10 were performed by comparing activities against the chromogenic peptide substrates Pyr-Phe-Leu-pNA and Bz-L-Arg-pNA (Peptides International, Louisville, Ky.). Assays were performed according to Kouzuma et al., (1996) J. Biochem 119: 1106-1113 in 100 mM sodium phosphate (pH 6.5), 0.3 M KCl, 0.1 M EDTA and 1 mM 100% DMSO with 500 µM of the peptide substrate. 1 µl of crude pro-c9 or pro-h10 and 1 µl of crude activated c9 and h10 were added to 100 µl of reaction solution containing either Pyr-Phe-Leu-pNA or Bz-L-Arg-pNA to look at substrate specificity. Supernatants from an uninduced sample were used as controls to eliminate potential Pichia protease contamination effects. Reactions were allowed to progress for 1 hr at 37° C., after which absorbance was measured at 410 nm. These studies demonstrated that both forms (pro and mature) of both enzymes have a specificity for Pyr-Phe-Leu-pNA. In contrast, the substrate Bz-L-Arg-pNA which is susceptible to cleavage by cathepsin B and cathepsin H was not hydrolyzed by either c9 or h10. This differential cleavage confirms that both c9 and h10 are cathepsin L-like proteases. No activity was observed with supernatant from the uninduced sample. The ability of the pro-cathepsins to hydrolyze Pyr-Phe-Leu-pNA was subsequently discovered to be the result of autoprocessing into the mature protease as a result of the slightly acidic pH (pH 6.5) of the reaction buffer. Both c9 and h10 were completely inhibited by E64 a general inhibitor of cathepsin proteases.

Example 4

Purification of c9 and h10 from Pichia Culture Supernatants

Media from small-scale culture supernatants from c9 or h10 expressing transformants (see Example 2) were diluted 1:4 with 50 mM Sodium carbonate buffer (pH 10). HPLC was performed on the sample using an Agilent 1100 (Agilent Technologies, Palo Alto, Calif.) with a HiTrap Q XL Cartridge (Amersham Biosciences, Piscataway, N.J.). A step gradient was run with Buffer A (50 mM Tris HCl, pH 8.0) and Buffer B (50 mM Tris HCL, pH 8.0, 1 M NaCl) at load conditions (0% Buffer B), 10% B, 20% B, 30% B, 40% B and 100% B at a flow rate of 0.7 ml/min. Flow through (FT) material and each step was collected as it eluted from the column based on UV absorbance. The FT and each step were tested for activity using the chromogenic substrate pyr-Phe-Leu-pNA (see Example 3) to identify c9 and h10 containing fractions. From the ability of fractions to hydrolyze the synthetic peptide substrate, h10 eluted in the load, 10% and 20% B samples and c9 eluted in the load, 20% and 30% B samples. SDS-PAGE was used to visualize c9 and h10 in each of the samples.

2.5 ml of each active step was concentrated 50 fold by loading the samples onto a Millipore Centricon 3 kD MWCO (molecular weight cut off) filter (Millipore Corporation, Billerica, Mass.) and centrifuging at 7500×g for 2 h at 4° C. This resulted in concentrating the volume remaining on top of the filter to about 200 µl. 200 µl of $H_2O$ was then added and the Centricon was centrifuged until a final volume of ~50 µl remained. The presence of c9 and h10 in the active steps was confirmed by their ability to hydrolyze Pyr-Phe-Leu-pNA and N-terminal amino acid sequence analysis.

Example 5

Digestion of Proteins by Purified c9 and h10 Cathepsin Proteases

β-casein and κ-casein (Sigma Chemical Co., St. Louis, Mo.) and Angiogenin (Bachem, 3700 Horizon Drive, King of Prussia, Pa., USA) were digested with purified c9 and h10 to identify potential cleavage recognition sites for these two western corn rootworm cathepsins. Cleavage time courses were performed in proteolysis buffer (100 mM sodium phosphate (pH 6.5), 0.3 M KCl, 0.1 M EDTA and 1 mM 100% DMSO) at 25° C., and reactions were stopped by addition of the inhibitor E-64 (3 µl 10 mM E-64 in 100 µl reaction volume). Digestion products were either separated by SDS-PAGE or used for LC-mass spectrometry to identify cleavage sites within the test protein/peptide substrates. In the case of SDS-PAGE, digestions were run on 12% NuPage polyacrylamide gels (Invitrogen) and digestion products transferred to PVDF membrane according to the instructions supplied by ProBlott™ membranes (Applied Biosystems Inc.). Protein bands were visualized by staining the transfer membrane with Ponceau S and visible bands were excised for N-terminal sequence analysis. When LC-mass spectrometry was used, 20 µl of the 100 µl digest reaction volume was injected into the Magic 2002 Microbore HPLC (Michrom Bioresources Inc., Auburn, Calif.) with a Magic C18 column (150 mm×1 mm; 200 Angstrom, 5 µm bead) linked to a Micromass mass spectrometer (Micromass, Beverly, Mass.) to obtain mass information on the digestion fragments. The remaining 80 µl of material was injected onto the Magic 2002 Microbore HPLC, and the peaks were collected for N-terminal sequencing.

The time course of β-casein digestion by c9 showed a major ~19 kD digestion product (indicated by black arrowhead) by 2 minutes after addition of enzyme. After 10 minutes two major digestion products were observed corresponding to the 19 kD fragment (from 2 min) and a new 16 kD fragment. Additional minor fragments were also observed at 10 min that were more abundant by 30 min, indicating a progressive cleavage of the 19 kD and 16 kD fragments into smaller fragments (indicated by gray arrowheads). N-terminal sequence analysis of the 19 kD and 16 kD fragments corresponded to the known N-terminus of β-casein (e.g., RELEELNVP; SEQ ID NO:18) indicating a C-terminal cleavage by c9. HPLC based isolation of the digestion products and subsequent N-terminal sequence analysis identified the primary and secondary cleavage sites to be after Ser166 (LS/QS; SEQ ID NO:2) and Leu140 (LL/QS; SEQ ID NO:19) respectively. Additional cleavage sites were observed for β-casein. The preference for a hydrophobic residue at the $P_2'$ position is consistent with known cleavage sites of cathepsin L proteases and in this case was biased toward Leu (L) (i.e., 5 of 6 occurrences). In all cases, a preference for a polar residue was observed at the $P_1'$ position with Gln (O) being the most prevalent (e.g. 4 of 6 occurrences).

κ-casein was also digested with c9 and h10 and recognition site specificity determined by the same methods used for β-casein. In the case of κ-casein major detectable cleavage sites were observed after Ser54, Asp62, Ser125, and Met127. Again, a preference for a hydrophobic residue at the $P_2'$ position was observed that was predominantly Leu (3 of 4 occurrences). Based on the available cleavage site information from β and κ casein, there appeared to be a strong bias towards Leu at the $P_2'$ position and a Gln residue at the $P_1'$ position. Since both the primary and secondary cleavage sites in β casein contained Gln-Ser at the $P_1'$ and $P_2'$ positions it was likely that Ser would be a good candidate for the $P_3$ position. Thus, the sequence Leu-X-Gln-Ser (LXQS; X=any amino acid; SEQ ID NO:1) was chosen as a cleavage sequence recognized by western corn rootworm cathepsins c9 and h10.

A peptide, angiogenin, available from Bachem (3700 Horizon Drive, King of Prussia, Pa.) was found to contain a sequence within it, LDQS (SEQ ID NO:20), that conformed to the LXQS (SEQ ID NO:1) motif defined above. Angiogenin was subjected to cleavage by c9 in proteolysis buffer (see above) for 30 or 60 min at 25° C. and the reaction was terminated by addition of E64. The identity of cleavage products was elucidated by LC-MS based on predicted molecular weights from the known angiogenin sequence. N-terminal sequence analysis was performed for confirmation of the LC-MS data. The results demonstrated that after 30 min two distinct pairs of cleavage products were detected that corresponded to cleavage immediately N-terminal to Leu8 or to Gln10. The relative sizes of the peaks indicated that cleavage at Gln10 (LD/QS; SEQ ID NO:20) was the primary preferred cleavage site. After digestion for 60 min, the sizes of the peaks corresponding to both cleavage products increased with LD/QS being the preferential cleavage recognition sequence. This demonstrated that c9 does effectively recognize the cleavage site LXQS (SEQ ID NO:1).

Example 6

Incorporation of LXQS at the Activation Site of Cry8 and Demonstration that Cry8 is Activated and Insecticidal After Ingestion by Western Corn Rootworm It is known that several Bt Cry proteins require an "activation" step for insecticidal activity in coleopteran. This activation step is in the form of a nick between helix 3 and helix 4 in domain 1 that results in a conformational change leading to insertion of domain 1 (led by helix 4) into the membrane. The two polypeptides created by the cleavage, however, remain associated under non-denaturing conditions. As demonstrated in U.S. patent application Ser. No. 10/606,320, entitled "Genes Encoding Proteins with Pesticidal Activity," filed Jun. 25, 2003, herein incorporated by reference, a modified Cry8 protein with the sequence FRRG (SEQ ID NO:21) or FRSRG (SEQ ID NO:22) inserted at amino acid 162 in the native Cry8 protein sequence renders the protein insecticidal without the requirement for activation by trypsin before insect ingestion. The functionality of the LXQS (SEQ ID NO:1) motif was tested by substituting a double LXQS motif (e.g., LXQSLXQS; SEQ ID NO:3) in place of FRRGFRRG (SEQ ID NO:23) in the Cry8Bb1 mutant K05 (SEQ ID NO:24 (nucleotide sequence); SEQ ID NO:25 (amino acid sequence)). In this case Ser was chosen for the X residue (e.g., LSQS; SEQ ID NO:2) as the primary cleavage site in β-casein contained a Ser in the $P_1'$ position. The resulting modified Cry8Bb1 protoxin was named ISC-1 (SEQ ID NO:26 (nucleotide sequence); SEQ ID NO:27 (amino acid sequence)).

Bioassay results on neonate western corn rootworm larvae were performed with 1 mg/ml of Cry8Bb1 mutants K04 (SEQ ID NO:28) and ISC-1 to compare their insecticidal activity. Cry8Bb1-K04 contains FRRGFRRG (SEQ ID NO:23) at amino acid 162 and has been previously demonstrated to be active at 1 mg/ml without the need for a pre-trypsinization step to activate Cry8. The results of the bioassays shown in Table 2 indicate that the sequence LSQSLSQS (SEQ ID NO:4) is recognized by western corn rootworm digestive proteases. Insecticidal activity is comparable to that of Cry8Bb1-K04. Moreover, the survivors from ISC-1 treated larvae were severely stunted compared to survivors from Cry8Bb1-K04.

TABLE 2

Bioassay results of Cry8Bb1-K04 compared to ISC-1.

| Sample (1 mg/ml) | Percent Mortality |
|---|---|
| Cry8 K04 | 47% (ms*) |
| ISC-1 | 43% (ss**) |

*survivors moderately stunted
**survivors severely stunted

Example 7

Resistance of LSQSLSQS Motif to Cleavage by Serine Proteases

Digestibilty

In order to confirm that the cathepsin-like motif LSQSLSQS (SEQ ID NO:4) was not susceptible to serine proteases (e.g., trypsin and chemotrypsin), 88 kDa polypeptides of Cry8Bb1-K05 (SEQ ID NO:25) and Cry8Bb1-ISC-1 (SEQ ID NO:27) were produced. Cry8Bb1-K05 has the FRRGFRRG motif (SEQ ID NO:23) in the activation loop that was previously shown to be cleaved by both serine proteases. Cry8Bb1-K05 was shown to be active in bioassays against WCRW, SCRW and CPB without prior activation by trypsin. Cry8Bb1-ISC-1 has the novel cathepsin-like protease motif LSQSLSQS (SEQ ID NO:4). Five micrograms of protein of each polypeptide was incubated with 1/50 (W/W) with trypsin and chemotrypsin at room temperature for 72 hours. SDS-PAGE analysis was then performed. As expected, results showed that Cry8Bb1-K05 was cleaved within the loop between helix 3 and 4 of domain I of the toxin molecule to generate a 55 kDa polypeptide. Cleavage of the activation loop between helix 3 and 4 was confirmed by N-terminal sequencing. In contrast, the 88 kDa Cry8Bb1-ISC-1 polypeptide was not cleaved within the activation loop to generate the 55 kDa polypeptide.

The same experiment was repeated using WCRW midgut juice in place of purified proteases. Data indicated that both toxin molecules were cleaved by a protease present in the WCRW midgut juice to produce the 55 kDa fragment.

Bioassays

The 88 KDa polypeptides of Cry8Bb1-K05 and Cry8Bb1-ISC-1 were then assayed for activity against WCRW, SCRW and CPB. Both toxins had significant activity against all three insects. These bioassays confirm that the 88 kDA polypeptide of Cry8Bb1-ISC-1 was as active as the 88 kDa polypeptide of Cry8Bb1-K05.

In summary, loop activation is critical for toxin activity. The above experiments demonstrate that the Cry8Bb1-ISC-188 kDa polypeptide is serine protease resistant but is still activated by midgut juice from a coleopteran insect. The novel motif LSQSLSQS (SEQ ID NO: 4) is therefore insect specific.

Example 8

Transformation and Regeneration of Transgenic Plants

Immature maize embryos from greenhouse donor plants are bombarded with a plasmid containing a nucleotide sequence encoding the modified Cry8Bb1 protoxin ISC-1 described herein above in Example 6 (SEQ ID NO:26) operably linked to the ubiquitin promoter and the selectable marker gene PAT (Wohlleben et al. (1988) Gene 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the modified Cry8 protoxin nucleotide sequence operably linked to the ubiquitin promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the modified Cry8 protoxin by assays known in the art, such as, for example, immunoassays and western blotting.

Analysis of Transgenic Maize Plants

Transgenic maize plants positive for expression of the modified Cry8Bb1 protoxin are tested for resistance to WCRW using standard bioassays known in the art. Such methods include, for example, root excision bioassays and whole plant bioassays. See, e.g., U.S. Patent Publication No. US 2003/0120054 and International Publication No. WO 03/018810.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 9

*Agrobacterium*-mediated Transformation of Maize

For *Agrobacterium*-mediated transformation of maize with the modified Cry8 protoxin of Example 7, the method of Zhao is employed (U.S. Pat. No. 5,981,840, and International Patent Publication No. WO 98/32326; the contents of which are hereby incorporated by reference). Briefly, immature embryos are isolated from maize and the embryos contacted with a suspension of *Agrobacterium*, where the bacteria are capable of transferring the modified Cry8 protoxin to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Transgenic maize plants positive for expression of the modified Cry8Bb1 protoxin are tested for resistance to WCRW, as described in Example 7.

Example 10

Soybean Embryo Transformation

Soybean embryos are bombarded with a plasmid containing the modified Cry8 protoxin of Example 7 operably linked to the ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050).

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the modified Cry8 protoxin operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 11

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 $\mu$E/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seeds are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids containing the modified Cry8 protoxin of Example 7 operably linked to the ubiquitin promoter are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% Sea-Plaque GTG agarose (BioWhitaker Molecular Applications) and the DNA fragments containing the modified Cry8 protoxin of Example 7 are cut from the agarose gel. DNA is purified from the agarose using the GELase digesting enzyme following the manufacturer's protocol.

A 50 $\mu$l aliquot of sterile distilled water containing 3 mg of gold particles (3 mg gold) is added to 5 $\mu$l of a 1 $\mu$g/$\mu$l DNA solution (either intact plasmid or DNA fragment prepared as described above), 50 $\mu$l 2.5M CaCl$_2$ and 20 $\mu$l of 0.1 M spermidine. The mixture is shaken 3 min on level 3 of a vortex shaker and spun for 10 sec in a bench microfuge. After a wash with 400 $\mu$l 100% ethanol the pellet is suspended by sonication in 40 $\mu$l of 100% ethanol. Five $\mu$l of DNA suspension is dispensed to each flying disk of the Biolistic PDS1000/HE instrument disk. Each 5 $\mu$l aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the desired phenotype. It should be noted that any detectable phenotype, resulting from the expression of the genes of interest, could be screened at this stage.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P,B,Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm |
| pH 5.8 | |

| FN Lite Stock Solutions | | |
|---|---|---|
| Stock # | 1000 ml | 500 ml |
| 1) MS Fe EDTA 100x Stock | | |
| Na2 EDTA* | 3.724 g | 1.862 g |
| FeSO4—7H2O | 2.784 g | 1.392 g |
| 2) MS Sulfate 100x stock | | |
| MgSO4—7H2O | 37.0 g | 18.5 g |
| MnSO4—H2O | 1.69 g | 0.845 g |
| ZnSO4—7H2O | 0.86 g | 0.43 g |
| CuSO4—5H2O | 0.0025 g | 0.00125 g |
| 3) FN Lite Halides 100x Stock | | |
| CaCl2—2H2O | 30.0 g | 15.0 g |
| KI | 0.083 g | 0.0715 g |
| CoCl2—6H2O | 0.0025 g | 0.00125 g |
| 4) FN Lite P,B,Mo 100x Stock | | |
| KH2PO4 | 18.5 g | 9.25 g |
| H3BO3 | 0.62 g | 0.31 g |
| Na2MoO4—2H2O | 0.025 g | 0.0125 g |

*Add first, dissolve in dark bottle while stirring

SB1 solid medium (per liter) comprises: 1 pkg. MS salts (Gibco/BRL—Cat# 11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat# 11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat# 11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat# 21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence encoding *Bacillus thuringiensis* Cry8Bb1 protoxin, wherein said Cry8Bb1 protoxin has at least one proteolytic activation site that has been engineered to comprise a cleavage site that is sensitive to an insect gut protease, wherein said proteolytic activation site comprises an amino acid sequence selected from the group consisting of LXQS (SEQ ID NO:1), LSQS (SEQ ID NO:2), LXQSLXQS (SEQ ID NO:3), and LSQSLSQS (SEQ ID NO:4), and wherein cleavage of said Cry8Bb1 protoxin by said insect gut protease produces an active Cry8Bb1 toxin or a variant thereof, wherein said variant has pesticidal activity and has at least 95% sequence identity to the amino acid sequence set forth in SEQ ID NO:11.

2. The isolated nucleic acid molecule of claim 1, wherein said proteolytic activation site comprises the amino acid sequence LXQS (SEQ ID NO:1).

3. The isolated nucleic acid molecule of claim 1, wherein said proteolytic activation site comprises the amino acid sequence LSQS (SEQ ID NO:2).

4. The isolated nucleic acid molecule of claim 1, wherein said proteolytic activation site comprises the amino acid sequence LXQSLXQS (SEQ ID NO:3).

5. The isolated nucleic acid molecule of claim 1, wherein said proteolytic activation site comprises the amino acid sequence LSQSLSQS (SEQ ID NO:4).

6. An expression cassette comprising the nucleic acid molecule of claim 1 operably linked to a promoter that drives expression in a plant.

7. A method for protecting a plant from an insect pest, said method comprising introducing into said plant at least one polynucleotide construct that comprises the nucleic acid molecule of claim 1 operably linked to a promoter that drives expression in said plant, wherein expression of said polynucleotide construct produces said Cry8Bb1 protoxin in said plant, wherein said insect pest ingests said plant and said Cry8Bb1 protoxin, and wherein cleavage of said Cry8Bb1 protoxin by said insect gut protease produces an active Cry8Bb1 toxin or a variant thereof, wherein said variant has pesticidal activity and has at least 95% sequence identity to the amino acid sequence set forth in SEQ ID NO: 11 insect.

8. The method of claim 7, wherein said proteolytic activation site comprises the amino acid sequence LXQS (SEQ ID NO:1).

9. The method of claim 7, wherein said proteolytic activation site comprises the amino acid sequence LSQS (SEQ ID NO:2).

10. The method of claim 7, wherein said proteolytic activation site comprises the amino acid sequence LXQSLXQS (SEQ ID NO:3).

11. The method of claim 7, wherein said proteolytic activation site comprises the amino acid sequence LSQSLSQS (SEQ ID NO:4).

12. The method of claim 7, wherein said Cry8Bb1 protoxin has improved pesticidal activity relative to a Cry8Bb1 protoxin that lacks said at least one engineered proteolytic activation site.

13. The method of claim 7, wherein said proteolytic activation site further stabilizes said Cry8Bb1 protoxin in the plant.

14. The method of claim 7, wherein said insect pest is selected from the group consisting of Colorado potato beetle, western corn rootworm, southern corn rootworm, northern corn rootworm, and boll weevil.

15. The method of claim 7, wherein said plant is a monocot.

16. The method of claim 15, wherein said monocot is maize.

17. The method of claim 7, wherein said plant is a dicot.

18. The method of claim 7, wherein said promoter is a root-preferred promoter.

19. The method of claim 7, wherein said insect gut protease is a cysteine protease.

20. The method of claim 19, wherein said cysteine protease is a cathepsin L-like protease.

21. A transformed plant comprising at least one polynucleotide construct that comprises the nucleic acid molecule of claim 1 operably linked to a promoter that drives expression in said plant.

22. The plant of claim 21, wherein said polynucleotide construct is stably incorporated into the genome of the plant.

23. A transgenic seed of the plant of claim 21, wherein the seed comprises said polynucleotide construct.

* * * * *

UNITED STATES PATENT AND TRADEMARK OFFICE
CERTIFICATE OF CORRECTION

PATENT NO. : 7,473,821 B2  
APPLICATION NO. : 11/448266  
DATED : January 6, 2009  
INVENTOR(S) : Abad et al.

Page 1 of 1

It is certified that error appears in the above-identified patent and that said Letters Patent is hereby corrected as shown below:

Column 18,  
Line 48, "≧90%" should read --≥90%--.

Column 32,  
Line 36, "saliva", both occurrences, should read --sativa--;  
Line 45, "cassaya" should read --cassava--;  
Line 60, "Omamentals" should read --Ornamentals--.

Column 33,  
Line 44, "fimgicides" should read --fungicides--.

Column 36,  
Line 25, "parvicorn is" should read --parvicornis--;  
Line 36, "Siphaflava" should read --Sipha flava--;  
Line 39, "two spotted" should read --twospotted--.

Column 37,  
Line 11, "*Agrotis*/psilon" should read --*Agrotis* ipsilon--.

Signed and Sealed this

Ninth Day of June, 2009

JOHN DOLL  
*Acting Director of the United States Patent and Trademark Office*

SEQUENCE LISTING

<160> NUMBER OF SEQ ID NOS: 28

<210> SEQ ID NO 1
<211> LENGTH: 4
<212> TYPE: PRT
<213> ORGANISM: Artificial Sequence
<220> FEATURE:

```
<223> OTHER INFORMATION: Proteolytic site
<220> FEATURE:
<221> NAME/KEY: VARIANT
<222> LOCATION: 2
<223> OTHER INFORMATION: Xaa = Any amino acid

<400> SEQUENCE: 1

Leu Xaa Gln Ser
 1

<210> SEQ ID NO 2
<211> LENGTH: 4
<212> TYPE: PRT
<213> ORGANISM: Artificial Sequence
<220> FEATURE:
<223> OTHER INFORMATION: Proteolytic site

<400> SEQUENCE: 2

Leu Ser Gln Ser
 1

<210> SEQ ID NO 3
<211> LENGTH: 8
<212> TYPE: PRT
<213> ORGANISM: Artificial Sequence
<220> FEATURE:
<223> OTHER INFORMATION: Proteolytic site
<220> FEATURE:
<221> NAME/KEY: VARIANT
<222> LOCATION: 2,6
<223> OTHER INFORMATION: Xaa = Any amino acid

<400> SEQUENCE: 3

Leu Xaa Gln Ser Leu Xaa Gln Ser
 1               5

<210> SEQ ID NO 4
<211> LENGTH: 8
<212> TYPE: PRT
<213> ORGANISM: Artificial Sequence
<220> FEATURE:
<223> OTHER INFORMATION: Proteolytic site

<400> SEQUENCE: 4

Leu Ser Gln Ser Leu Ser Gln Ser
 1               5

<210> SEQ ID NO 5
<211> LENGTH: 4
<212> TYPE: PRT
<213> ORGANISM: Artificial Sequence
<220> FEATURE:
<223> OTHER INFORMATION: Amino acid sequence located between alpha
      helices 3 and 4 of domain 1 of Cry8Bb1 toxin

<400> SEQUENCE: 5

Asn Gly Ser Arg
 1

<210> SEQ ID NO 6
<211> LENGTH: 1035
<212> TYPE: DNA
<213> ORGANISM: Diabrotica virgifera virgifera

<400> SEQUENCE: 6
gaaaaatcag aatgaagctg ttcatccttg ccgctgccct tattgtggcc acaagtgcca      60
atctaggtgc cttcgaaaaa tggaccagtt ttaaggcaac ccataacaaa tcttacaacg     120
```

-continued

```
ttattgaaga caaacttcgt ttcgctgttt tccaagacaa cctcaaaaaa atcgaggaac    180
acaatgctaa atacgaaagt ggagaagaaa cctactactt ggctgttaac aaattcgccg    240
attggtccag cgctgaattc caagctatgt tggcccgtca gatggctaac aagcccaaac    300
aatcctttat tgcaaaacac gtagccgatc ccaatgtcca agctgtagaa gaagttgatt    360
ggagagatat gccgtttg ggagtcaaag atcaaggaca gtgtggatca tgctgggctt    420
tcagtaccac cggatccctc gaaggtcaac tcgccatcca caaaaatcaa cgtgttcctc    480
tcagtgaaca agaattggta gactgtgaca catcaagaaa tgctggttgt aacggaggtt    540
tgatgacaga tgcctttaac tatgttaaac gccatggtct ctcttccgaa tctcaatatg    600
catacaccgg cagagatgat cgctgcaaga atgttgagaa caaaccactc tcttccatta    660
gtggctacgt agaacttgaa acaactgaag atgcactcgc gtccgctgtt gctagcgtag    720
gtccagtttc catcgctgtt gatgctgata catggcaatt atacggaggt ggacttttca    780
acaacaaaaa ctgtagaacc aacctcaatc acggtgttct tgctgttgga tacactaaag    840
atgcattcat tgtcaagaac tcatggggaa ctagctgggg tgaacaaggt tacatcagag    900
ttgcccgtgg tgaaaacttg tgtggtatta acctcatgaa ctcttaccct aaattgtaaa    960
tgatttaatg caaatgaaac accaaataga attcaaaaat aaagataaat aaaaaactaa   1020
aaaaaaaaaa aaaaa                                                    1035
```

<210> SEQ ID NO 7
<211> LENGTH: 315
<212> TYPE: PRT
<213> ORGANISM: Diabrotica virgifera virgifera

<400> SEQUENCE: 7

```
Met Lys Leu Phe Ile Leu Ala Ala Ala Leu Ile Val Ala Thr Ser Ala
 1               5                  10                  15

Asn Leu Gly Ala Phe Glu Lys Trp Thr Ser Phe Lys Ala Thr His Asn
            20                  25                  30

Lys Ser Tyr Asn Val Ile Glu Asp Lys Leu Arg Phe Ala Val Phe Gln
        35                  40                  45

Asp Asn Leu Lys Lys Ile Glu Glu His Asn Ala Lys Tyr Glu Ser Gly
    50                  55                  60

Glu Glu Thr Tyr Tyr Leu Ala Val Asn Lys Phe Ala Asp Trp Ser Ser
65                  70                  75                  80

Ala Glu Phe Gln Ala Met Leu Ala Arg Gln Met Ala Asn Lys Pro Lys
                85                  90                  95

Gln Ser Phe Ile Ala Lys His Val Ala Asp Pro Asn Val Gln Ala Val
            100                 105                 110

Glu Glu Val Asp Trp Arg Asp Ser Ala Val Leu Gly Val Lys Asp Gln
        115                 120                 125

Gly Gln Cys Gly Ser Cys Trp Ala Phe Ser Thr Thr Gly Ser Leu Glu
    130                 135                 140

Gly Gln Leu Ala Ile His Lys Asn Gln Arg Val Pro Leu Ser Glu Gln
145                 150                 155                 160

Glu Leu Val Asp Cys Asp Thr Ser Arg Asn Ala Gly Cys Asn Gly Gly
                165                 170                 175

Leu Met Thr Asp Ala Phe Asn Tyr Val Lys Arg His Gly Leu Ser Ser
            180                 185                 190

Glu Ser Gln Tyr Ala Tyr Thr Gly Arg Asp Asp Arg Cys Lys Asn Val
        195                 200                 205
```

```
Glu Asn Lys Pro Leu Ser Ser Ile Ser Gly Tyr Val Glu Leu Glu Thr
    210                 215                 220

Thr Glu Asp Ala Leu Ala Ser Ala Val Ala Ser Val Gly Pro Val Ser
225                 230                 235                 240

Ile Ala Val Asp Ala Asp Thr Trp Gln Leu Tyr Gly Gly Gly Leu Phe
                245                 250                 255

Asn Asn Lys Asn Cys Arg Thr Asn Leu Asn His Gly Val Leu Ala Val
            260                 265                 270

Gly Tyr Thr Lys Asp Ala Phe Ile Val Lys Asn Ser Trp Gly Thr Ser
        275                 280                 285

Trp Gly Glu Gln Gly Tyr Ile Arg Val Ala Arg Gly Glu Asn Leu Cys
290                 295                 300

Gly Ile Asn Leu Met Asn Ser Tyr Pro Lys Leu
305                 310                 315

<210> SEQ ID NO 8
<211> LENGTH: 1034
<212> TYPE: DNA
<213> ORGANISM: Diabrotica virgifera virgifera

<400> SEQUENCE: 8
ttttagtgag agaaaactca aaatgaagct gttaattcta gccgccaccc tcattgtggc      60
cataaatgcc aatttatctg cctttgagca atggaccagt tttaaggcaa cacacaacaa    120
attttacaac gttattgagg acaaacttcg ttttgctgtt ttccaagaga atctccgcaa    180
aatcgacgca cacaatgcta atacgaaaa gggagaagaa acctactaca tggctgttaa    240
caaattcgcc gattggtcca gcgcagaatt ccaagccatg ttggaccgtc agatggctaa    300
caagccaaaa caatccttca ttgcaaaaca cgtagtcgat cccaatgtcc aagctgtaga    360
agaagttgat tggagagaaa gtgctgtttt gggagtcaaa gatcaaggac agtgtggatc    420
atgctgggct ttcagtacca ccggatccct cgaaggtcaa ctcgccatcc acaaaaatca    480
acgtgttcct ctcagtgaac aagaattggt agactgtgat aaggtaaacg atggttgtga    540
cggaggtttg atgacagatg ccttcttta tattgaacat catggtcttt catcagaaga    600
acaatacccc tatacaggcg tagatggtca ttgcaatcat gtaaaagaca aacaagtctc    660
ttcgatcagt ggttacgtcg aacttgatga aactgaaagt gctctagctg atgctctcgc    720
taatgttggt ccagtgtcaa tagctgtcga agctgataca tggcaattct attcaggtgg    780
agttttcaac aataaaaatt gtggagacgc tcttaaccac ggtgttcttg ctgtgggata    840
cactaaagat gtcttcatcg ttaaaaactc atggggaaca ggctggggtg aacaaggtta    900
catcagagtt gcccgtggta gcaacttatg tggtattaac ctcatgaact cttaccccaa    960
gttgtagata acagttaatg aaagtgata tatttataat aataaatgat ataaattaca  1020
aaaaaaaaaa aaaa                                                     1034

<210> SEQ ID NO 9
<211> LENGTH: 314
<212> TYPE: PRT
<213> ORGANISM: Diabrotica virgifera virgifera

<400> SEQUENCE: 9

Met Lys Leu Leu Ile Leu Ala Ala Thr Leu Ile Val Ala Ile Asn Ala
1               5                   10                  15

Asn Leu Ser Ala Phe Glu Gln Trp Thr Ser Phe Lys Ala Thr His Asn
            20                  25                  30
```

```
Lys Phe Tyr Asn Val Ile Glu Asp Lys Leu Arg Phe Ala Val Phe Gln
             35                  40                  45
Glu Asn Leu Arg Lys Ile Asp Ala His Asn Ala Lys Tyr Glu Lys Gly
     50                  55                  60
Glu Glu Thr Tyr Tyr Met Ala Val Asn Lys Phe Ala Asp Trp Ser Ser
 65                  70                  75                  80
Ala Glu Phe Gln Ala Met Leu Asp Arg Gln Met Ala Asn Lys Pro Lys
                 85                  90                  95
Gln Ser Phe Ile Ala Lys His Val Val Asp Pro Asn Val Gln Ala Val
            100                 105                 110
Glu Glu Val Asp Trp Arg Glu Ser Ala Val Leu Gly Val Lys Asp Gln
            115                 120                 125
Gly Gln Cys Gly Ser Cys Trp Ala Phe Ser Thr Gly Ser Leu Glu
        130                 135                 140
Gly Gln Leu Ala Ile His Lys Asn Gln Arg Val Pro Leu Ser Glu Gln
145                 150                 155                 160
Glu Leu Val Asp Cys Asp Lys Val Asn Asp Gly Cys Asp Gly Gly Leu
                165                 170                 175
Met Thr Asp Ala Phe Phe Tyr Ile Glu His His Gly Leu Ser Ser Glu
            180                 185                 190
Glu Gln Tyr Pro Tyr Thr Gly Val Asp Gly His Cys Asn His Val Lys
        195                 200                 205
Asp Lys Gln Val Ser Ser Ile Ser Gly Tyr Val Glu Leu Asp Glu Thr
    210                 215                 220
Glu Ser Ala Leu Ala Asp Ala Leu Ala Asn Val Gly Pro Val Ser Ile
225                 230                 235                 240
Ala Val Glu Ala Asp Thr Trp Gln Phe Tyr Ser Gly Gly Val Phe Asn
                245                 250                 255
Asn Lys Asn Cys Gly Asp Ala Leu Asn His Gly Val Leu Ala Val Gly
            260                 265                 270
Tyr Thr Lys Asp Val Phe Ile Val Lys Asn Ser Trp Gly Thr Gly Trp
        275                 280                 285
Gly Glu Gln Gly Tyr Ile Arg Val Ala Arg Gly Ser Asn Leu Cys Gly
    290                 295                 300
Ile Asn Leu Met Asn Ser Tyr Pro Lys Leu
305                 310

<210> SEQ ID NO 10
<211> LENGTH: 3621
<212> TYPE: DNA
<213> ORGANISM: Bacillus thuringiensis

<400> SEQUENCE: 10
atgagtccaa ataatcaaaa tgaatatgaa attatagatg cgacaccttc tacttctgta      60
tccaatgatt ctaacagata cccttttgcg aatgagccaa caaatgcgct acaaaatatg     120
gattataaag attatttaaa aatgtctgcg ggaaatgcta gtgaataccc tggttcacct     180
gaagtacttg ttagcggaca agatgcagct aaggccgcaa ttgatatagt aggtaaatta     240
ctatcaggtt tagggtgccc atttgttggg ccgatagtga gtctttatac tcaacttatt     300
gatattctgt ggccttcagg ggaaaagagt caatgggaaa ttttttatgga acaagtagaa     360
gaactcatta atcaaaaaat agcagaatat gcaggaata aagcgctttc ggaattagaa     420
ggattaggta taattacca attatatcta actgcgcttg aagaatggga agaaaatcca     480
```

```
aatggttcaa gagccttacg agatgtgcga aatcgatttg aaatcctgga tagtttattt      540
acgcaatata tgccatcttt tagagtgaca aattttgaag taccattcct tactgtatat      600
gcaatggcag ccaaccttca tttactgtta ttaaaggacg cgtcaatttt tggagaagaa      660
tggggatggt caacaactac tattaataac tattatgatc gtcaaatgaa acttactgca      720
gaatattctg atcactgtgt aaagtggtat gaaactggtt tagcaaaatt aaaaggcacg      780
agcgctaaac aatgggttga ctataaccaa ttccgtagag aaatgacact ggcggtttta      840
gatgttgttg cattattccc aaattatgac acacgcacgt acccaatgga acgaaagca       900 caactaacaa gggaagtata tacagatcca ctgggcgcgg taaacgtgtc ttcaattggt      960
tcctggtatg acaaagcacc ttctttcgga gtgatagaat catccgttat tcgaccaccc     1020
catgtatttg attatataac gggactcaca gtgtatacac aatcaagaag catttcttcc     1080
gctcgctata aagacattg ggctggtcat caaataagct accatcgtgt cagtaggggt      1140
agtaatcttc aacaaatgta tggaactaat caaaatctac acagcactag tacctttgat     1200
tttacgaatt atgatattta caagactcta tcaaggatg cagtactcct tgatattgtt      1260
taccctggtt atacgtatat attttttgga atgccagaag tcgagttttt catggtaaac     1320
caattgaata ataccagaaa gacgttaaag tataatccag tttccaaaga tattatagcg     1380
agtacaagag attcggaatt agaattacct ccagaaactt cagatcaacc aaattatgag     1440
tcatatagcc atagattatg tcatatcaca agtattcccg cgacgggtaa cactaccgga     1500
ttagtacctg tattttcttg gacacatcga agtgcagatt taaacaatac aatatattca     1560
gataaaatca ctcaaattcc ggccgttaaa tgttgggata atttaccgtt tgttccagtg     1620
gtaaaaggac caggacatac aggagggat ttattacagt ataatagaag tactggttct      1680
gtaggaacct tatttctagc tcgatatggc ctagcattag aaaaagcagg gaaatatcgt     1740
gtaagactga gatatgctac tgatgcagat attgtattgc atgtaaacga tgctcagatt     1800
cagatgccaa aaacaatgaa cccaggtgag gatctgacat ctaaaacttt taaagttgca     1860
gatgctatca caacattaaa tttagcaaca gatagttcgc tagcattgaa acataattta     1920
ggtgaagacc ctaattcaac attatctggt atagtttacg ttgaccgaat cgaattcatc     1980
ccagtagatg agacatatga agcggaacaa gatttagaag cagcgaagaa agcagtgaat     2040
gccttgttta cgaatacaaa agatggctta cgaccaggcg taacggatta tgaagtgaat     2100
caagcggcaa acttagtgga atgcctatcg gatgatttgt atccaaatga aaaacgattg     2160
ttatttgatg cagtgagaga ggcaaaacgc ctcagtgagg cacgtaattt gcttcaagat     2220
ccagatttcc aagagataaa tggagaaaat ggctggacgg caagtacggg aattgaggtt     2280
atagaagggg atgctttatt caaagggcgt tatctacgcc taccaggtgc gagagaaata     2340
gatacggaaa cgtatccaac gtatctgtat caaaaagtag aggaaggtgt attaaaacca     2400
tacacaagat atagattgag agggtttgtc ggaagcagtc aaggattgga aattttcaca     2460
attcgtcatc aaacgaaccg aattgtaaaa aatgtaccgg atgatttgct gccagatgta     2520
tctcctgtta actcggatgg tagtatcaat cgatgcagcg aacaaaagta tgtgaatagc     2580
cgtttagaag tagaaaaccg ttctggtgaa gcgcatgagt tctctattcc tattgataca     2640
ggtgaaatcg attacaatga aaatgcagga atatgggttg gatttaagat tacggaccca     2700
gagggatatg caacactcgg aaacctagaa ttggtcgaag agggaccttt atcaggagac     2760
gcattagaac gcttgcaaag agaagaacaa cagtggaaga ttcaaaatgac aagaagacgt     2820 gaagaaacag atagaaggta tatggcatcg aaacaagcgg tagatcgttt atatgccgat     2880
```

-continued

```
tatcaggatc agcaactgaa tcctgatgta gagattacag atcttactgc ggcccaagat    2940
ctgatacagt ccattcctta cgtatataac gaaatgttcc cagaaatacc agggatgaac    3000
tatacgaagt ttacagaatt aacagatcga ctccaacaag cgtggagttt gtatgatcag    3060
cgaaatgcca taccaaatgg tgattttcga atgggttaa gtaattggaa tgcaacgcct     3120
ggcgtagaag tacaacaaat caatcataca tctgtccttg tgattccaaa ctgggatgag    3180
caagtttcgc aacagtttac agttcaaccg aatcaaagat atgtgttacg agttactgcg    3240
agaaaagaag gggtaggaaa tggatatgta agtatccgtg atggtggaaa tcaaacagaa    3300
acgcttactt ttagtgcaag cgattatgat acaaatggaa tgtataatac gcaagtgtcc    3360
aatacaaatg gatataacac aaataatgcg tataatacac aagcatcgag tacaaacgga    3420
tataacgcaa ataatatgta taatacgcaa gcatcgaata caaacggata taacacaaat    3480
agtgtgtaca atgatcaaac cggctatatc acaaaaacag tgacattcat cccgtataca    3540
gatcaaatgt ggattgagat gagtgagaca gaaggtacat tctatataga agtgtagaa     3600 ttgattgtag acgtagagta a                                              3621
```

<210> SEQ ID NO 11
<211> LENGTH: 1206
<212> TYPE: PRT
<213> ORGANISM: Bacillus thuringiensis

<400> SEQUENCE: 11

```
Met Ser Pro Asn Asn Gln Asn Glu Tyr Glu Ile Ile Asp Ala Thr Pro
  1               5                  10                  15

Ser Thr Ser Val Ser Asn Asp Ser Asn Arg Tyr Pro Phe Ala Asn Glu
             20                  25                  30

Pro Thr Asn Ala Leu Gln Asn Met Asp Tyr Lys Asp Tyr Leu Lys Met
         35                  40                  45

Ser Ala Gly Asn Ala Ser Glu Tyr Pro Gly Ser Pro Glu Val Leu Val
     50                  55                  60

Ser Gly Gln Asp Ala Ala Lys Ala Ala Ile Asp Ile Val Gly Lys Leu
 65                  70                  75                  80

Leu Ser Gly Leu Gly Val Pro Phe Val Gly Pro Ile Val Ser Leu Tyr
                 85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Ala Met Ala Ala Asn Leu His Leu
        195                 200                 205

Leu Leu Leu Lys Asp Ala Ser Ile Phe Gly Glu Glu Trp Gly Trp Ser
    210                 215                 220

Thr Thr Thr Ile Asn Asn Tyr Tyr Asp Arg Gln Met Lys Leu Thr Ala
225                 230                 235                 240
```

-continued

```
Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Ala Val Leu Asp Val Val Ala Leu Phe Pro Asn
        275                 280                 285

Tyr Asp Thr Arg Thr Tyr Pro Met Glu Thr Lys Ala Gln Leu Thr Arg
    290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Val Ser Arg Gly Ser Asn Leu Gln
    370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Tyr Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Lys Tyr Asn Pro Val Ser Lys Asp Ile Ile Ala Ser Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Asn Thr Thr Gly Leu Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Cys Trp Asp Asn Leu Pro Phe Val Pro Val Lys Gly Pro
    530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
                565                 570                 575

Gly Lys Tyr Arg Val Arg Leu Arg Tyr Ala Thr Asp Ala Asp Ile Val
            580                 585                 590

Leu His Val Asn Asp Ala Gln Ile Gln Met Pro Lys Thr Met Asn Pro
        595                 600                 605

Gly Glu Asp Leu Thr Ser Lys Thr Phe Lys Val Ala Asp Ala Ile Thr
    610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655
```

```
Ile Glu Phe Ile Pro Val Asp Glu Thr Tyr Glu Ala Glu Gln Asp Leu
            660                 665                 670

Glu Ala Ala Lys Lys Ala Val Asn Ala Leu Phe Thr Asn Thr Lys Asp
            675                 680                 685

Gly Leu Arg Pro Gly Val Thr Asp Tyr Glu Val Asn Gln Ala Ala Asn
            690                 695                 700

Leu Val Glu Cys Leu Ser Asp Asp Leu Tyr Pro Asn Glu Lys Arg Leu
705                 710                 715                 720

Leu Phe Asp Ala Val Arg Glu Ala Lys Arg Leu Ser Glu Ala Arg Asn
            725                 730                 735

Leu Leu Gln Asp Pro Asp Phe Gln Glu Ile Asn Gly Glu Asn Gly Trp
            740                 745                 750

Thr Ala Ser Thr Gly Ile Glu Val Ile Glu Gly Asp Ala Leu Phe Lys
            755                 760                 765

Gly Arg Tyr Leu Arg Leu Pro Gly Ala Arg Glu Ile Asp Thr Glu Thr
            770                 775                 780

Tyr Pro Thr Tyr Leu Tyr Gln Lys Val Glu Glu Gly Val Leu Lys Pro
785                 790                 795                 800

Tyr Thr Arg Tyr Arg Leu Arg Gly Phe Val Gly Ser Ser Gln Gly Leu
            805                 810                 815

Glu Ile Phe Thr Ile Arg His Gln Thr Asn Arg Ile Val Lys Asn Val
            820                 825                 830

Pro Asp Asp Leu Leu Pro Asp Val Ser Pro Val Asn Ser Asp Gly Ser
            835                 840                 845

Ile Asn Arg Cys Ser Glu Gln Lys Tyr Val Asn Ser Arg Leu Glu Val
            850                 855                 860

Glu Asn Arg Ser Gly Glu Ala His Glu Phe Ser Ile Pro Ile Asp Thr
865                 870                 875                 880

Gly Glu Ile Asp Tyr Asn Glu Asn Ala Gly Ile Trp Val Gly Phe Lys
            885                 890                 895

Ile Thr Asp Pro Glu Gly Tyr Ala Thr Leu Gly Asn Leu Glu Leu Val
            900                 905                 910

Glu Glu Gly Pro Leu Ser Gly Asp Ala Leu Glu Arg Leu Gln Arg Glu
            915                 920                 925

Glu Gln Gln Trp Lys Ile Gln Met Thr Arg Arg Arg Glu Glu Thr Asp
            930                 935                 940

Arg Arg Tyr Met Ala Ser Lys Gln Ala Val Asp Arg Leu Tyr Ala Asp
945                 950                 955                 960

Tyr Gln Asp Gln Gln Leu Asn Pro Asp Val Glu Ile Thr Asp Leu Thr
            965                 970                 975

Ala Ala Gln Asp Leu Ile Gln Ser Ile Pro Tyr Val Tyr Asn Glu Met
            980                 985                 990

Phe Pro Glu Ile Pro Gly Met Asn Tyr Thr Lys Phe Thr Glu Leu Thr
            995                 1000                1005

Asp Arg Leu Gln Gln Ala Trp Ser Leu Tyr Asp Gln Arg Asn Ala Ile
            1010                1015                1020

Pro Asn Gly Asp Phe Arg Asn Gly Leu Ser Asn Trp Asn Ala Thr Pro
1025                1030                1035                1040

Gly Val Glu Val Gln Gln Ile Asn His Thr Ser Val Leu Val Ile Pro
            1045                1050                1055

Asn Trp Asp Glu Gln Val Ser Gln Gln Phe Thr Val Gln Pro Asn Gln
            1060                1065                1070

Arg Tyr Val Leu Arg Val Thr Ala Arg Lys Glu Gly Val Gly Asn Gly
```

-continued

```
               1075                1080                1085
Tyr Val Ser Ile Arg Asp Gly Gly Asn Gln Thr Glu Thr Leu Thr Phe
    1090                1095                1100
Ser Ala Ser Asp Tyr Asp Thr Asn Gly Met Tyr Asn Thr Gln Val Ser
1105                1110                1115                1120
Asn Thr Asn Gly Tyr Asn Thr Asn Asn Ala Tyr Asn Thr Gln Ala Ser
            1125                1130                1135
Ser Thr Asn Gly Tyr Asn Ala Asn Asn Met Tyr Asn Thr Gln Ala Ser
            1140                1145                1150
Asn Thr Asn Gly Tyr Asn Thr Asn Ser Val Tyr Asn Asp Gln Thr Gly
        1155                1160                1165
Tyr Ile Thr Lys Thr Val Thr Phe Ile Pro Tyr Thr Asp Gln Met Trp
    1170                1175                1180
Ile Glu Met Ser Glu Thr Glu Gly Thr Phe Tyr Ile Glu Ser Val Glu
1185                1190                1195                1200
Leu Ile Val Asp Val Glu
            1205

<210> SEQ ID NO 12
<211> LENGTH: 3633
<212> TYPE: DNA
<213> ORGANISM: Bacillus thuringiensis

<400> SEQUENCE: 12
```

| | | | | | |
|---|---|---|---|---|---|
| atgagtccaa | ataatcaaaa | tgaatatgaa | attatagatg | cgacaccttc | tacttctgta | 60 |
| tccaatgatt | ctaacagata | cccttttgcg | aatgagccaa | caaatgcgct | acaaaatatg | 120 |
| gattataaag | attatttaaa | aatgtctgcg | ggaaatgcta | gtaataccc | tggttcacct | 180 |
| gaagtacttg | ttagcggaca | agatgcagct | aaggccgcaa | ttgatatagt | aggtaaatta | 240 |
| ctatcaggtt | tagggtcccc | atttgttggg | ccgatagtga | gtctttatac | tcaacttatt | 300 |
| gatattctgt | ggccttcagg | gcaaaagagt | caatgggaga | tttttatgga | acaagtagaa | 360 |
| gaactcataa | atcaaaaaat | agcagaatat | gcaggaaata | aagcgctttc | ggaattagaa | 420 |
| ggattaggta | taattacca | attatatcta | actgcgcttg | aagaatggaa | agaaaatcca | 480 |
| aatggttcaa | gagccttacg | agatgtgcga | atcgatttg | aaatcctgga | tagtttattt | 540 |
| acgcaataca | tgccatcttt | tcgagtgaca | aattttgaag | taccattcct | tacagtatat | 600 |
| acacaggcag | ccaaccttca | tttactgtta | ttaaaggacg | cttcaatttt | tggagaagaa | 660 |
| tggggatggt | ctacaaccac | tattaataac | tattatgatc | gtcaaatgaa | acttactgca | 720 |
| gaatattctg | atcactgtgt | aaagtggtat | gaaactggtt | tagcaaaatt | aaaaggcacg | 780 |
| agcgctaaac | aatgggtcga | ctataaccaa | ttccgtagag | aaatgacact | gacggtttta | 840 |
| gatgttgttg | cattattccc | aaattatgac | acacgcacgt | acccaatgga | aacgaaagca | 900 |
| caactaacaa | gggaagtata | tacagatcca | ctgggcgcgg | taaacgtgtc | ttcaattggt | 960 |
| tcctggtatg | acaaagcacc | ttcttcgga | gtgatagaat | catccgttat | tcgaccaccc | 1020 |
| catgtatttg | attatataac | gggactcaca | gtgtatacac | aatcaagaag | catttcttcc | 1080 |
| gctcgctata | taagacattg | gctggtcat | caaataagct | atcatcggat | ttttagtgat | 1140 |
| aatattataa | aacagatgta | tggaactaat | caaaatctac | acagcactag | taccttttgat | 1200 |
| tttacgaatt | atgatattta | caagacgtta | tcaaagatg | cggtgctcct | tgatattgtt | 1260 |
| tttcctggtt | atacgtatat | atttttttgga | atgccagaag | tcgagttttt | catggtaaac | 1320 |
| caattgaata | ataccagaaa | gacgttaaag | tataatccgg | tttccaaaga | tattataagcg | 1380 |

```
gggacaagag attcggaatt agaattacct ccagaaactt cagatcaacc aaattatgag    1440
tcatatagcc atagattatg tcatatcaca agtattcccg cgacgggttc aactaccgga    1500
ttagtacctg tattttcttg gacacatcgg agtgccgatc ttataaatgc agttcattca    1560
gataaaatta ctcagattcc ggtcgtaaag gtttctgatt tggctccctc tataacagga    1620
gggccaaata ataccgttgt atcgggtcct ggatttacag gggggggat aataaaagta     1680 ataagaaatg gagtaattat atcacatatg cgtgttaaaa tttcagacat taacaaagaa    1740
tatagtatga ggattcggta tgcttccgct aataatactg aattttatat aaatccttct    1800
gaagaaaacg ttaaatctca cgctcaaaaa actatgaata gaggtgaagc tttaacatat    1860
aataaattta attatgcgac tttgccccct attaaattta cgacaaccga acctttcatt    1920
actctagggg ctatatttga agcggaagac tttcttggaa ttgaagctta tatagaccga    1980
atcgaattta tcccagtaga tgagacatat gaagcggaac aagatttaga agcagcgaag    2040
aaagcagtga atgccttgtt tacgaataca aaagatggct tacgaccagg cgtaacggat    2100
tatgaagtga atcaagcggc aaacttagtg gaatgcctat cggatgattt gtatccaaat    2160
gaaaaacgat tgttatttga tgcagtgaga gaggcaaaac gcctcagtga ggcacgtaat    2220
ttgcttcaag atccagattt ccaagagata aatggagaaa atggctggac ggcaagtacg    2280
ggaattgagg ttatagaagg ggatgcttta ttcaaagggc gttatctacg cctaccaggt    2340
gcgagagaaa tagatacgga aacgtatcca acgtatctgt atcaaaaagt agaggaaggt    2400
gtattaaaac catacacaag atatagattg agagggtttg tcggaagcag tcaaggattg    2460
gaaattttca caattcgtca tcaaacgaac cgaattgtaa aaaatgtacc ggatgatttg    2520
ctgccagatg tatctcctgt taactcggat ggtagtatca atcgatgcag cgaacaaaag    2580
tatgtgaata gccgtttaga agtagaaaac cgttctggtg aagcgcatga gttctctatt    2640
cctattgata caggtgaaat cgattacaat gaaaatgcag gaatatgggt tggatttaag    2700
attacggacc cagagggata tgcaacactc ggaaacctag aattggtcga agagggacct    2760
ttatcaggag acgcattaga acgcttgcaa agagaagaac aacagtggaa gattcaaatg    2820
acaagaagac gtgaagaaac agatagaagg tatatggcat cgaaacaagc ggtagatcgt    2880
ttatatgccg attatcagga tcagcaactg aatcctgatg tagagattac agatcttact    2940
gcggcccaag atctgataca gtccattcct tacgtatata acgaaatgtt cccagaaata    3000
ccagggatga actatacgaa gtttacagaa ttaacagatc gactccaaca agcgtggagt    3060
ttgtatgatc agcgaaatgc cataccaaat ggtgattttc gaaatgggtt aagtaattgg    3120
aatgcaacgc ctggcgtaga agtacaacaa atcaatcata catctgtcct tgtgattcca    3180
aactgggatg agcaagtttc gcaacagttt acagttcaac cgaatcaaag atatgtgtta    3240
cgagttactg cgagaaaaga aggggtagga aatggatatg taagtatccg tgatggtgga    3300
aatcaaacag aaacgcttac ttttagtgca agcgattatg atacaaatgg aatgtataat    3360
acgcaagtgt ccaatacaaa tggatataac acaaataatg cgtataatac acaagcatcg    3420
agtacaaacg gatataacgc aaataatatg tataatacgc aagcatcgaa tacaaacgga    3480
tataacacaa atagtgtgta caatgatcaa accggctata tcacaaaaac agtgacattc    3540
atcccgtata cagatcaaat gtggattgag atgagtgaga cagaaggtac attctatata    3600
gaaagtgtag aattgattgt agacgtagag taa                                 3633
```

<210> SEQ ID NO 13

-continued

```
<211> LENGTH: 1210
<212> TYPE: PRT
<213> ORGANISM: Bacillus thuringiensis

<400> SEQUENCE: 13

Met Ser Pro Asn Asn Gln Asn Glu Tyr Glu Ile Ile Asp Ala Thr Pro
  1               5                  10                  15

Ser Thr Ser Val Ser Asn Asp Ser Asn Arg Tyr Pro Phe Ala Asn Glu
             20                  25                  30

Pro Thr Asn Ala Leu Gln Asn Met Asp Tyr Lys Asp Tyr Leu Lys Met
         35                  40                  45

Ser Ala Gly Asn Ala Ser Glu Tyr Pro Gly Ser Pro Glu Val Leu Val
 50                  55                  60

Ser Gly Gln Asp Ala Ala Lys Ala Ala Ile Asp Ile Val Gly Lys Leu
 65                  70                  75                  80

Leu Ser Gly Leu Gly Val Pro Phe Val Gly Pro Ile Val Ser Leu Tyr
                 85                  90                  95

Thr Gln Leu Ile Asp Ile Leu Trp Pro Ser Gly Gln Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Gln Ala Ala Asn Leu His Leu
        195                 200                 205

Leu Leu Leu Lys Asp Ala Ser Ile Phe Gly Glu Glu Trp Gly Trp Ser
210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Thr Val Leu Asp Val Val Ala Leu Phe Pro Asn
        275                 280                 285

Tyr Asp Thr Arg Thr Tyr Pro Met Glu Thr Lys Ala Gln Leu Thr Arg
290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Ile Phe Ser Asp Asn Ile Ile Lys
370                 375                 380

Gln Met Tyr Gly Thr Asn Gln Asn Leu His Ser Thr Ser Thr Phe Asp
```

-continued

```
            385                 390                 395                 400
Phe Thr Asn Tyr Asp Ile Tyr Lys Thr Leu Ser Lys Asp Ala Val Leu
                405                 410                 415

Leu Asp Ile Val Phe Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
            435                 440                 445

Leu Lys Tyr Asn Pro Val Ser Lys Asp Ile Ile Ala Gly Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
            485                 490                 495

Ser Thr Thr Gly Leu Val Pro Val Phe Ser Trp Thr His Arg Ser Ala
            500                 505                 510

Asp Leu Ile Asn Ala Val His Ser Asp Lys Ile Thr Gln Ile Pro Val
            515                 520                 525

Val Lys Val Ser Asp Leu Ala Pro Ser Ile Thr Gly Gly Pro Asn Asn
            530                 535                 540

Thr Val Ser Gly Pro Gly Phe Thr Gly Gly Ile Ile Lys Val
545                 550                 555                 560

Ile Arg Asn Gly Val Ile Ile Ser His Met Arg Val Lys Ile Ser Asp
                565                 570                 575

Ile Asn Lys Glu Tyr Ser Met Arg Ile Arg Tyr Ala Ser Ala Asn Asn
            580                 585                 590

Thr Glu Phe Tyr Ile Asn Pro Ser Glu Glu Asn Val Lys Ser His Ala
            595                 600                 605

Gln Lys Thr Met Asn Arg Gly Glu Ala Leu Thr Tyr Asn Lys Phe Asn
            610                 615                 620

Tyr Ala Thr Leu Pro Pro Ile Lys Phe Thr Thr Glu Pro Phe Ile
625                 630                 635                 640

Thr Leu Gly Ala Ile Phe Glu Ala Glu Asp Phe Leu Gly Ile Glu Ala
                645                 650                 655

Tyr Ile Asp Arg Ile Glu Phe Ile Pro Val Asp Glu Thr Tyr Glu Ala
                660                 665                 670

Glu Gln Asp Leu Glu Ala Ala Lys Lys Ala Val Asn Ala Leu Phe Thr
            675                 680                 685

Asn Thr Lys Asp Gly Leu Arg Pro Gly Val Thr Asp Tyr Glu Val Asn
            690                 695                 700

Gln Ala Ala Asn Leu Val Glu Cys Leu Ser Asp Asp Leu Tyr Pro Asn
705                 710                 715                 720

Glu Lys Arg Leu Leu Phe Asp Ala Val Arg Glu Ala Lys Arg Leu Ser
                725                 730                 735

Glu Ala Arg Asn Leu Leu Gln Asp Pro Asp Phe Gln Glu Ile Asn Gly
            740                 745                 750

Glu Asn Gly Trp Thr Ala Ser Thr Gly Ile Glu Val Ile Glu Gly Asp
            755                 760                 765

Ala Leu Phe Lys Gly Arg Tyr Leu Arg Leu Pro Gly Ala Arg Glu Ile
            770                 775                 780

Asp Thr Glu Thr Tyr Pro Thr Tyr Leu Tyr Gln Lys Val Glu Glu Gly
785                 790                 795                 800

Val Leu Lys Pro Tyr Thr Arg Tyr Arg Leu Arg Gly Phe Val Gly Ser
                805                 810                 815
```

-continued

```
Ser Gln Gly Leu Glu Ile Phe Thr Ile Arg His Gln Thr Asn Arg Ile
            820                 825                 830
Val Lys Asn Val Pro Asp Asp Leu Leu Pro Asp Val Ser Pro Val Asn
        835                 840                 845
Ser Asp Gly Ser Ile Asn Arg Cys Ser Glu Gln Lys Tyr Val Asn Ser
    850                 855                 860
Arg Leu Glu Val Glu Asn Arg Ser Gly Glu Ala His Glu Phe Ser Ile
865                 870                 875                 880
Pro Ile Asp Thr Gly Glu Ile Asp Tyr Asn Glu Asn Ala Gly Ile Trp
            885                 890                 895
Val Gly Phe Lys Ile Thr Asp Pro Glu Gly Tyr Ala Thr Leu Gly Asn
        900                 905                 910
Leu Glu Leu Val Glu Glu Gly Pro Leu Ser Gly Asp Ala Leu Glu Arg
    915                 920                 925
Leu Gln Arg Glu Glu Gln Gln Trp Lys Ile Gln Met Thr Arg Arg Arg
930                 935                 940
Glu Glu Thr Asp Arg Arg Tyr Met Ala Ser Lys Gln Ala Val Asp Arg
945                 950                 955                 960
Leu Tyr Ala Asp Tyr Gln Asp Gln Gln Leu Asn Pro Asp Val Glu Ile
            965                 970                 975
Thr Asp Leu Thr Ala Ala Gln Asp Leu Ile Gln Ser Ile Pro Tyr Val
        980                 985                 990
Tyr Asn Glu Met Phe Pro Glu Ile Pro Gly Met Asn Tyr Thr Lys Phe
    995                 1000                1005
Thr Glu Leu Thr Asp Arg Leu Gln Gln Ala Trp Ser Leu Tyr Asp Gln
    1010                1015                1020
Arg Asn Ala Ile Pro Asn Gly Asp Phe Arg Asn Gly Leu Ser Asn Trp
1025                1030                1035                1040
Asn Ala Thr Pro Gly Val Glu Val Gln Gln Ile Asn His Thr Ser Val
            1045                1050                1055
Leu Val Ile Pro Asn Trp Asp Glu Gln Val Ser Gln Gln Phe Thr Val
        1060                1065                1070
Gln Pro Asn Gln Arg Tyr Val Leu Arg Val Thr Ala Arg Lys Glu Gly
    1075                1080                1085
Val Gly Asn Gly Tyr Val Ser Ile Arg Asp Gly Gly Asn Gln Thr Glu
    1090                1095                1100
Thr Leu Thr Phe Ser Ala Ser Asp Tyr Asp Thr Asn Gly Met Tyr Asn
1105                1110                1115                1120
Thr Gln Val Ser Asn Thr Asn Gly Tyr Asn Thr Asn Asn Ala Tyr Asn
            1125                1130                1135
Thr Gln Ala Ser Ser Thr Asn Gly Tyr Asn Ala Asn Asn Met Tyr Asn
        1140                1145                1150
Thr Gln Ala Ser Asn Thr Asn Gly Tyr Asn Thr Asn Ser Val Tyr Asn
    1155                1160                1165
Asp Gln Thr Gly Tyr Ile Thr Lys Thr Val Thr Phe Ile Pro Tyr Thr
    1170                1175                1180
Asp Gln Met Trp Ile Glu Met Ser Glu Thr Glu Gly Thr Phe Tyr Ile
1185                1190                1195                1200
Glu Ser Val Glu Leu Ile Val Asp Val Glu
            1205                1210

<210> SEQ ID NO 14
<211> LENGTH: 39
```

```
<212> TYPE: DNA
<213> ORGANISM: Artificial Sequence
<220> FEATURE:
<223> OTHER INFORMATION: Forward PCR primer for h10 protease

<400> SEQUENCE: 14
cgactcgaga aaagaaatct aggtgccttc gaaaaatgg                              39

<210> SEQ ID NO 15
<211> LENGTH: 42
<212> TYPE: DNA
<213> ORGANISM: Artificial Sequence
<220> FEATURE:
<223> OTHER INFORMATION: Reverse PCR primer for h10 protease

<400> SEQUENCE: 15
ccattatatg cggccgccta caatttaggg taagagttca tg                          42

<210> SEQ ID NO 16
<211> LENGTH: 38
<212> TYPE: DNA
<213> ORGANISM: Artificial Sequence
<220> FEATURE:
<223> OTHER INFORMATION: Forward PCR primer for c9 protease

<400> SEQUENCE: 16
cgactcgaga aagaaattta tctgcctttg agcaatgg                               38

<210> SEQ ID NO 17
<211> LENGTH: 39
<212> TYPE: DNA
<213> ORGANISM: Artificial Sequence
<220> FEATURE:
<223> OTHER INFORMATION: Reverse PCR primer for c9 protease

<400> SEQUENCE: 17
cctatattag cggccgccta caacttgggg taagagttc                              39

<210> SEQ ID NO 18
<211> LENGTH: 9
<212> TYPE: PRT
<213> ORGANISM: Artificial Sequence
<220> FEATURE:
<223> OTHER INFORMATION: N-terminal fragment of beta-casein

<400> SEQUENCE: 18

Arg Glu Leu Glu Glu Leu Asn Val Pro
 1               5

<210> SEQ ID NO 19
<211> LENGTH: 4
<212> TYPE: PRT
<213> ORGANISM: Artificial Sequence
<220> FEATURE:
<223> OTHER INFORMATION: Proteolytic site

<400> SEQUENCE: 19

Leu Leu Gln Ser
 1

<210> SEQ ID NO 20
<211> LENGTH: 4
<212> TYPE: PRT
<213> ORGANISM: Artificial Sequence
<220> FEATURE:
<223> OTHER INFORMATION: Proteolytic site
```

-continued

<400> SEQUENCE: 20

Leu Asp Gln Ser
1

<210> SEQ ID NO 21
<211> LENGTH: 4
<212> TYPE: PRT
<213> ORGANISM: Artificial Sequence
<220> FEATURE:
<223> OTHER INFORMATION: Proteolytic site

<400> SEQUENCE: 21

Phe Arg Arg Gly
1

<210> SEQ ID NO 22
<211> LENGTH: 5
<212> TYPE: PRT
<213> ORGANISM: Artificial Sequence
<220> FEATURE:
<223> OTHER INFORMATION: Proteolytic site

<400> SEQUENCE: 22

Phe Arg Ser Arg Gly
1 5

<210> SEQ ID NO 23
<211> LENGTH: 8
<212> TYPE: PRT
<213> ORGANISM: Artificial Sequence
<220> FEATURE:
<223> OTHER INFORMATION: Proteolytic site

<400> SEQUENCE: 23

Phe Arg Arg Gly Phe Arg Arg Gly
1 5

<210> SEQ ID NO 24
<211> LENGTH: 2433
<212> TYPE: DNA
<213> ORGANISM: Artificial Sequence
<220> FEATURE:
<223> OTHER INFORMATION: Modified Cry8Bb1 gene (Cry8Bb1-K05)

<400> SEQUENCE: 24
atgagtccaa ataatcaaaa tgaatatgaa attatagatg cgacaccttc tacttctgta 60
tccaatgatt ctaacagata cccttttgcg aatgagccaa caaatgcgct acaaaatatg 120
gattataaag attatttaaa aatgtctgcg ggaaatgcta gtgaataccc tggttcacct 180
gaagtacttg ttagcggaca agatgcagct aaggccgcaa ttgatatagt aggtaaatta 240
ctatcaggtt taggggtccc atttgttggg ccgatagtga gtctttatac tcaacttatt 300
gatattctgt ggccttcagg ggaaaagagt caatgggaaa tttttatgga acaagtagaa 360
gaactcatta atcaaaaaat agcagaatat gcaaggaata aagcgctttc ggaattagaa 420
ggattaggta ataattacca attatatcta actgcgcttg aagaatggga agaaaatcca 480
tttcgacgag gttttcgacg aggtgcctta cgagatgtgc gaaatcgatt tgaaatcctg 540
gatagtttat ttacgcaata tatgccatct tttagagtga caaattttga agtaccattc 600
cttactgtat atgcaatggc agccaacctt catttactgt tattaaagga cgcgtcaatt 660
tttggagaag aatggggatg gtcaacaact actattaata actattatga tcgtcaaatg 720
aaacttactg cagaatattc tgatcactgt gtaaagtggt atgaaactgg tttagcaaaa 780

```
ttaaaaggca cgagcgctaa acaatgggtt gactataacc aattccgtag agaaatgaca    840
ctggcggttt tagatgttgt tgcattattc ccaaattatg acacacgcac gtacccaatg    900
gaaacgaaag cacaactaac aagggaagta tatacagatc cactgggcgc ggtaaacgtg    960
tcttcaattg gttcctggta tgacaaagca ccttctttcg gagtgataga atcatccgtt   1020
attcgaccac cccatgtatt tgattatata acgggactca cagtgtatac acaatcaaga   1080
agcatttctt ccgctcgcta tataagacat tgggctggtc atcaaataag ctaccatcgt   1140
gtcagtaggg gtagtaatct tcaacaaatg tatggaacta atcaaaatct acacagcact   1200
agtacctttg attttacgaa ttatgatatt tacaagactc tatcaaagga tgcagtactc   1260
cttgatattg tttaccctgg ttatacgtat atatttttg gaatgccaga agtcgagttt    1320
ttcatggtaa accaattgaa taataccaga aagacgttaa agtataatcc agtttccaaa   1380
gatattatag cgagtacaag agattcggaa ttagaattac ctccagaaac ttcagatcaa   1440
ccaaattatg agtcatatag ccatagatta tgtcatatca caagtattcc cgcgacgggt   1500
aacactaccg gattagtacc tgtatttcct tggacacatc gaagtgcaga tttaaacaat   1560
acaatatatt cagataaaat cactcaaatt ccggccgtta atgttggga taatttaccg    1620
tttgttccag tggtaaaagg accaggacat acaggagggg atttattaca gtataataga   1680
agtactggtt ctgtaggaac cttatttcta gctcgatatg gcctagcatt agaaaaagca   1740
gggaaatatc gtgtaagact gagatatgct actgatgcag atattgtatt gcatgtaaac   1800
gatgctcaga ttcagatgcc aaaaacaatg aacccaggtg aggatctgac atctaaaact   1860
tttaaagttg cagatgctat cacaacagta aatttagcaa cagatagttc ggtagcagtg   1920
aaacataatg taggtgaaga ccctaattca acagtatctg gtatagttta cgttgaccga   1980
atcgaattca tcccagtaga tgagacatat gaagcggaag cagcgaagtt tcgacgtggt   2040
tttcgacgtg gtaaagcagt gaatgccttg tttacgaata caaaagatgg cttacgacca   2100
ggcgtaacgg attatgaagt gaatcaagcg gcaaacttag tggaatgcct atcggatgat   2160
ttgtatccaa atgaaaaacg attgttattt gatgcagtga gagaggcaaa acgcctcagt   2220
gaggcacgta atttgcttca agatccagat ttccaagaga taaatggaga aaatggctgg   2280
acggcaagta cggaattgaa ggttatagaa ggggatgctt tattcaaagg gcgttatcta   2340
cgcctaccag gtgcgagaga aatagatacg gaaacgtatc caacgtatct gtatcaaaaa   2400
gtagaggaag gtgtattaaa accatagctc gag                                2433
```

<210> SEQ ID NO 25  
<211> LENGTH: 786  
<212> TYPE: PRT  
<213> ORGANISM: Artificial Sequence  
<220> FEATURE:  
<223> OTHER INFORMATION: Modified Cry8Bb1 polypeptide (Cry8Bb1-K05)

<400> SEQUENCE: 25

```
Met Ser Pro Asn Asn Gln Asn Glu Tyr Glu Ile Ile Asp Ala Thr Pro
 1               5                  10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60
```

```
Ser Gly Gln Asp Ala Ala Lys Ala Ala Ile Asp Ile Val Gly Lys Leu
 65                  70                  75                  80

Leu Ser Gly Leu Gly Val Pro Phe Val Gly Pro Ile Val Ser Leu Tyr
                 85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
            115                 120                 125

Glu Tyr Ala Arg Asn Lys Ala Leu Ser Glu Leu Glu Gly Leu Gly Asn
            130                 135                 140

Asn Tyr Gln Leu Tyr Leu Thr Ala Leu Glu Glu Trp Glu Glu Asn Pro
145                 150                 155                 160

Phe Arg Arg Gly Phe Arg Arg Gly Ala Leu Arg Asp Val Arg Asn Arg
                165                 170                 175

Phe Glu Ile Leu Asp Ser Leu Phe Thr Gln Tyr Met Pro Ser Phe Arg
            180                 185                 190

Val Thr Asn Phe Glu Val Pro Phe Leu Thr Val Tyr Ala Met Ala Ala
            195                 200                 205

Asn Leu His Leu Leu Leu Lys Asp Ala Ser Ile Phe Gly Glu Glu
            210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
                260                 265                 270

Asn Gln Phe Arg Arg Glu Met Thr Leu Ala Val Leu Asp Val Val Ala
                275                 280                 285

Leu Phe Pro Asn Tyr Asp Thr Arg Thr Tyr Pro Met Glu Thr Lys Ala
            290                 295                 300

Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
                325                 330                 335

Glu Ser Ser Val Ile Arg Pro Pro His Val Phe Asp Tyr Ile Thr Gly
            340                 345                 350

Leu Thr Val Tyr Thr Gln Ser Arg Ser Ile Ser Ser Ala Arg Tyr Ile
            355                 360                 365

Arg His Trp Ala Gly His Gln Ile Ser Tyr His Arg Val Ser Arg Gly
            370                 375                 380

Ser Asn Leu Gln Gln Met Tyr Gly Thr Asn Gln Asn Leu His Ser Thr
385                 390                 395                 400

Ser Thr Phe Asp Phe Thr Asn Tyr Asp Ile Tyr Lys Thr Leu Ser Lys
            405                 410                 415

Asp Ala Val Leu Leu Asp Ile Val Tyr Pro Gly Tyr Thr Tyr Ile Phe
            420                 425                 430

Phe Gly Met Pro Glu Val Glu Phe Phe Met Val Asn Gln Leu Asn Asn
            435                 440                 445

Thr Arg Lys Thr Leu Lys Tyr Asn Pro Val Ser Lys Asp Ile Ile Ala
            450                 455                 460

Ser Thr Arg Asp Ser Glu Leu Glu Leu Pro Pro Glu Thr Ser Asp Gln
465                 470                 475                 480

Pro Asn Tyr Glu Ser Tyr Ser His Arg Leu Cys His Ile Thr Ser Ile
```

-continued

```
                485                 490                 495

Pro Ala Thr Gly Asn Thr Thr Gly Leu Val Pro Val Phe Ser Trp Thr
            500                 505                 510

His Arg Ser Ala Asp Leu Asn Asn Thr Ile Tyr Ser Asp Lys Ile Thr
        515                 520                 525

Gln Ile Pro Ala Val Lys Cys Trp Asp Asn Leu Pro Phe Val Pro Val
    530                 535                 540

Val Lys Gly Pro Gly His Thr Gly Gly Asp Leu Leu Gln Tyr Asn Arg
545                 550                 555                 560
Ser Thr Gly Ser Val Gly Thr Leu Phe Leu Ala Arg Tyr Gly Leu Ala
                565                 570                 575

Leu Glu Lys Ala Gly Lys Tyr Arg Val Arg Leu Arg Tyr Ala Thr Asp
            580                 585                 590

Ala Asp Ile Val Leu His Val Asn Asp Ala Gln Ile Gln Met Pro Lys
        595                 600                 605

Thr Met Asn Pro Gly Glu Asp Leu Thr Ser Lys Thr Phe Lys Val Ala
    610                 615                 620

Asp Ala Ile Thr Thr Val Asn Leu Ala Thr Asp Ser Ser Val Ala Val
625                 630                 635                 640
Lys His Asn Val Gly Glu Asp Pro Asn Ser Thr Val Ser Gly Ile Val
                645                 650                 655

Tyr Val Asp Arg Ile Glu Phe Ile Pro Val Asp Glu Thr Tyr Glu Ala
            660                 665                 670

Glu Gln Asp Leu Glu Ala Ala Lys Phe Arg Arg Gly Phe Arg Arg Gly
        675                 680                 685

Lys Ala Val Asn Ala Leu Phe Thr Asn Thr Lys Asp Gly Leu Arg Pro
    690                 695                 700

Gly Val Thr Asp Tyr Glu Val Asn Gln Ala Ala Asn Leu Val Glu Cys
705                 710                 715                 720
Leu Ser Asp Asp Leu Tyr Pro Asn Glu Lys Arg Leu Leu Phe Asp Ala
                725                 730                 735

Val Arg Glu Ala Lys Arg Leu Ser Glu Ala Arg Asn Leu Leu Gln Asp
            740                 745                 750

Pro Asp Phe Gln Glu Ile Asn Gly Glu Asn Gly Trp Thr Ala Ser Thr
        755                 760                 765

Gly Ile Glu Val Ile Glu Gly Asp Ala Leu Phe Lys Gly Arg Tyr Leu
    770                 775                 780

Arg Leu
785
```

<210> SEQ ID NO 26
<211> LENGTH: 2399
<212> TYPE: DNA
<213> ORGANISM: Artificial Sequence
<220> FEATURE:
<223> OTHER INFORMATION: Modified Cry8Bb1 gene (Cry8Bb1-ISC-1)

<400> SEQUENCE: 26

```
ccggatccgc catggccccg aacaaccaga acgagtacga gatcatcgac gccaccccga     60
gcaccagcgt gagcaacgac agcaaccgct acccgttcgc caacgagccg accaacgccc    120
tgcagaacat ggactacaag gactacctca agatgagcgc cggcaacgcc agcgagtacc    180
cgggcagccc ggaggtgctg gtgagcggcc aggacgccgc caaggccgcc atcgacatcg    240
tgggcaagct cctgagcggc ctcggcgtgc cgttcgtggg cccgatcgtg agcctgtaca    300
```

-continued

```
cccagctcat cgacatcctg tggccgagcg gcgagaagag ccagtgggag atcttcatgg      360
agcaggtgga ggaactgatc aaccagaaga tcgcggaata cgcgcgcaat aaggcgctgt      420
cggaactgga aggcctgggc aataattacc agctgtacct gaccgcgctg aagagtggg       480
aagagaatcc gctgtcgcag tcgctgtcgc agagcgcgct ggtggacgtg cgcaatcgct      540
tcgaaatcct ggactcgctg ttcacccagt acatgccctc cttccgcgtg accaatttcg      600
aagtgccgtt cctgacggtg tatgcgatgg cggcgaatct gcacctgctg ctgctgaagg      660
acgcgtctat cttcggcgaa gaatgggct ggtcaacgac gacgatcaat aattattatg       720
accgccagat gaagctgacg gcggaatata gtgaccactg cgtgaagtgg tatgaaacgg      780
gcctggccaa gctgaagggc acgagcgcga acagtgggt ggattataat caattccgcc       840
gcgaaatgac gctcgccgtg ctggatgtgg tggccttgtt cccgaattat gatacgcgca      900
cctatccgat ggaaacgaaa gcccaactga cccgcgaagt ttataccgat ccgctcggcg      960
ccgttaatgt cagcagcatc ggcagctggt atgataaagc cccgagcttc ggcgtgatcg      1020
agtcgtccgt tattcgcccg ccgcatgtct tcgattatat taccggcttg accgtctata     1080
cccaatctcg ctcaattagt agcgcccggt atatacggca ttgggccggc catcaaatat      1140
cgtatcatcg cgtctcccgg ggctctaatc tgcaacaaat gtatgggacc aatcagaatc     1200
tgcactcaac cagtaccttc gacttcacca attacgatat ctacaagacc ctgagcaaag     1260
acgccgtcct gctcgatata gtctaccccg gctacaccta catcttcttc gggatgccag     1320
aagtcgagtt cttcatggtc aatcagctga ataacacgcg caagacactg aaatacaatc     1380
ctgtctcgaa agatattata gcctccactc gcgattctga gctcgagctt ccgcccgaga     1440
cctcagatca accaaaactac gagagttaca gccatgccct atgccacatc acgtcgatcc    1500
ctgccacagg caacactacc ggcttagtcc cggtcttctc ctggacgcac cgctctgccg     1560
atctgaacaa cacaatctac tcagataaga tcactcagat tcccgccgtc aaatgttggg     1620
ataacctgcc attcgtgcct gtggtgaagg gcccggggca caccggaggt gacctgctcc     1680
agtacaaccg gagtacgggc agcgtcggga cattgtttct tgcccgctac ggactagcct     1740
tagagaaagc cggcaagtac agagtgcgtc tgcgatacgc gactgatgct gacattgttc     1800
tccacgtaaa cgacgcacag attcagatgc ccaagaccat gaacccaggc gaggacttga     1860
cgtcgaagac attcaaggtc gccgacgcga ttactaccgt caaccttgct acggactcct     1920
ctgtcgcggt caagcacaac gtgggggagg accctaactc aacagttagc ggaattgtat     1980
acgtcgaccg catcgagttc atcccggtgg acgagactta cgaggccgag caggacctag     2040
aggcggctaa gttccggagg ggtttcagac gtggcaaggc agtcaacgcc ttattcacca     2100
acacgaagga cgggctgcga cccggagtaa cagactacga ggtcaaccag gcggctaacc     2160
tcgtggagtg cttgtcggac gacctttacc caaacgagaa gcgcctgctc ttcgacgcag     2220
ttcgggaggc caagaggttg tccgaggcga gaaaccttct gcaggaccct gacttccagg     2280
agatcaacgg tgagaacggc tggactgctt ctactgggat cgaggtaatc gagggagatg     2340
ctctgttcaa gggtagatac cttagacttt aggtcatgag tcatgagtca gttaactag      2399
```

<210> SEQ ID NO 27
<211> LENGTH: 786
<212> TYPE: PRT
<213> ORGANISM: Artificial Sequence
<220> FEATURE:
<223> OTHER INFORMATION: Modified Cry8Bb1 polypeptide (Cry8Bb1-ISC-1)

<400> SEQUENCE: 27

-continued

```
Met Ser Pro Asn Asn Gln Asn Glu Tyr Glu Ile Ile Asp Ala Thr Pro
 1               5                  10                  15

Ser Thr Ser Val Ser Asn Asp Ser Asn Arg Tyr Pro Phe Ala Asn Glu
             20                  25                  30

Pro Thr Asn Ala Leu Gln Asn Met Asp Tyr Lys Asp Tyr Leu Lys Met
         35                  40                  45

Ser Ala Gly Asn Ala Ser Glu Tyr Pro Gly Ser Pro Glu Val Leu Val
 50                  55                  60

Ser Gly Gln Asp Ala Ala Lys Ala Ala Ile Asp Ile Val Gly Lys Leu
 65                  70                  75                  80

Leu Ser Gly Leu Gly Val Pro Phe Val Gly Pro Ile Val Ser Leu Tyr
                 85                  90                  95

Thr Gln Leu Ile Asp Ile Leu Trp Pro Ser Gly Glu Lys Ser Gln Trp
             100                 105                 110

Glu Ile Phe Met Glu Gln Val Glu Glu Leu Ile Asn Gln Lys Ile Ala
         115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Glu Glu Asn Pro
145                 150                 155                 160

Leu Ser Gln Ser Leu Ser Gln Ser Ala Leu Arg Asp Val Arg Asn Arg
                165                 170                 175

Phe Glu Ile Leu Asp Ser Leu Phe Thr Gln Tyr Met Pro Ser Phe Arg
            180                 185                 190

Val Thr Asn Phe Glu Val Pro Phe Leu Thr Val Tyr Ala Met Ala Ala
        195                 200                 205

Asn Leu His Leu Leu Leu Lys Asp Ala Ser Ile Phe Gly Glu Glu
    210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
            260                 265                 270

Asn Gln Phe Arg Arg Glu Met Thr Leu Ala Val Leu Asp Val Val Ala
        275                 280                 285

Leu Phe Pro Asn Tyr Asp Thr Arg Thr Tyr Pro Met Glu Thr Lys Ala
    290                 295                 300

Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
                325                 330                 335

Glu Ser Ser Val Ile Arg Pro Pro His Val Phe Asp Tyr Ile Thr Gly
            340                 345                 350

Leu Thr Val Tyr Thr Gln Ser Arg Ser Ile Ser Ser Ala Arg Tyr Ile
        355                 360                 365

Arg His Trp Ala Gly His Gln Ile Ser Tyr His Arg Val Ser Arg Gly
    370                 375                 380

Ser Asn Leu Gln Gln Met Tyr Gly Thr Asn Gln Asn Leu His Ser Thr
385                 390                 395                 400

Ser Thr Phe Asp Phe Thr Asn Tyr Asp Ile Tyr Lys Thr Leu Ser Lys
                405                 410                 415
```

```
Asp Ala Val Leu Leu Asp Ile Val Tyr Pro Gly Tyr Thr Tyr Ile Phe
            420                 425                 430

Phe Gly Met Pro Glu Val Glu Phe Met Val Asn Gln Leu Asn Asn
        435                 440                 445

Thr Arg Lys Thr Leu Lys Tyr Asn Pro Val Ser Lys Asp Ile Ile Ala
    450                 455                 460

Ser Thr Arg Asp Ser Glu Leu Glu Leu Pro Glu Thr Ser Asp Gln
465                 470                 475                 480

Pro Asn Tyr Glu Ser Tyr Ser His Arg Leu Cys His Ile Thr Ser Ile
                485                 490                 495

Pro Ala Thr Gly Asn Thr Thr Gly Leu Val Pro Val Phe Ser Trp Thr
            500                 505                 510

His Arg Ser Ala Asp Leu Asn Asn Thr Ile Tyr Ser Asp Lys Ile Thr
        515                 520                 525

Gln Ile Pro Ala Val Lys Cys Trp Asp Asn Leu Pro Phe Val Pro Val
    530                 535                 540

Val Lys Gly Pro Gly His Thr Gly Gly Asp Leu Leu Gln Tyr Asn Arg
545                 550                 555                 560

Ser Thr Gly Ser Val Gly Thr Leu Phe Leu Ala Arg Tyr Gly Leu Ala
                565                 570                 575

Leu Glu Lys Ala Gly Lys Tyr Arg Val Arg Leu Arg Tyr Ala Thr Asp
            580                 585                 590

Ala Asp Ile Val Leu His Val Asn Asp Ala Gln Ile Gln Met Pro Lys
        595                 600                 605

Thr Met Asn Pro Gly Glu Asp Leu Thr Ser Lys Thr Phe Lys Val Ala
    610                 615                 620

Asp Ala Ile Thr Thr Val Asn Leu Ala Thr Asp Ser Ser Val Ala Val
625                 630                 635                 640

Lys His Asn Val Gly Glu Asp Pro Asn Ser Thr Val Ser Gly Ile Val
                645                 650                 655

Tyr Val Asp Arg Ile Glu Phe Ile Pro Val Asp Glu Thr Tyr Glu Ala
            660                 665                 670

Glu Gln Asp Leu Glu Ala Ala Lys Phe Arg Arg Gly Phe Arg Arg Gly
        675                 680                 685

Lys Ala Val Asn Ala Leu Phe Thr Asn Thr Lys Asp Gly Leu Arg Pro
    690                 695                 700

Gly Val Thr Asp Tyr Glu Val Asn Gln Ala Ala Asn Leu Val Glu Cys
705                 710                 715                 720

Leu Ser Asp Asp Leu Tyr Pro Asn Glu Lys Arg Leu Leu Phe Asp Ala
                725                 730                 735

Val Arg Glu Ala Lys Arg Leu Ser Glu Ala Arg Asn Leu Leu Gln Asp
            740                 745                 750

Pro Asp Phe Gln Glu Ile Asn Gly Glu Asn Gly Trp Thr Ala Ser Thr
        755                 760                 765

Gly Ile Glu Val Ile Glu Gly Asp Ala Leu Phe Lys Gly Arg Tyr Leu
    770                 775                 780

Arg Leu
785

<210> SEQ ID NO 28
<211> LENGTH: 673
<212> TYPE: PRT
<213> ORGANISM: Artificial Sequence
<220> FEATURE:
<223> OTHER INFORMATION: Modified Cry8Bb1 polypeptide (Cry8Bb1-K04)
```

```
<400> SEQUENCE: 28

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Glu Glu Asn Pro
145                 150                 155                 160

Phe Arg Arg Gly Phe Arg Arg Gly Ala Leu Arg Asp Val Arg Asn Arg
                165                 170                 175

Phe Glu Ile Leu Asp Ser Leu Phe Thr Gln Tyr Met Pro Ser Phe Arg
            180                 185                 190

Val Thr Asn Phe Glu Val Pro Phe Leu Thr Val Tyr Ala Met Ala Ala
        195                 200                 205

Asn Leu His Leu Leu Leu Leu Lys Asp Ala Ser Ile Phe Gly Glu Glu
210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
            260                 265                 270

Asn Gln Phe Arg Arg Glu Met Thr Leu Ala Val Leu Asp Val Val Ala
        275                 280                 285

Leu Phe Pro Asn Tyr Asp Thr Arg Thr Tyr Pro Met Glu Thr Lys Ala
290                 295                 300

Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
                325                 330                 335

Glu Ser Ser Val Ile Arg Pro Pro His Val Phe Asp Tyr Ile Thr Gly
            340                 345                 350

Leu Thr Val Tyr Thr Gln Ser Arg Ser Ile Ser Ser Ala Arg Tyr Ile
        355                 360                 365

Arg His Trp Ala Gly His Gln Ile Ser Tyr Arg Val Ser Arg Gly
370                 375                 380

Ser Asn Leu Gln Gln Met Tyr Gly Thr Asn Gln Asn Leu His Ser Thr
385                 390                 395                 400

Ser Thr Phe Asp Phe Thr Asn Tyr Asp Ile Tyr Lys Thr Leu Ser Lys
```

-continued

```
                      405                    410                    415
Asp Ala Val Leu Leu Asp Ile Val Tyr Pro Gly Tyr Thr Tyr Ile Phe
            420                    425                    430

Phe Gly Met Pro Glu Val Glu Phe Phe Met Val Asn Gln Leu Asn Asn
            435                    440                    445

Thr Arg Lys Thr Leu Lys Tyr Asn Pro Val Ser Lys Asp Ile Ile Ala
            450                    455                    460

Ser Thr Arg Asp Ser Glu Leu Glu Leu Pro Pro Glu Thr Ser Asp Gln
465                     470                    475                    480

Pro Asn Tyr Glu Ser Tyr Ser His Arg Leu Cys His Ile Thr Ser Ile
                485                    490                    495

Pro Ala Thr Gly Asn Thr Thr Gly Leu Val Pro Val Phe Ser Trp Thr
                500                    505                    510

His Arg Ser Ala Asp Leu Asn Asn Thr Ile Tyr Ser Asp Lys Ile Thr
                515                    520                    525

Gln Ile Pro Ala Val Lys Cys Trp Asp Asn Leu Pro Phe Val Pro Val
        530                    535                    540

Val Lys Gly Pro Gly His Thr Gly Gly Asp Leu Leu Gln Tyr Asn Arg
545                     550                    555                    560

Ser Thr Gly Ser Val Gly Thr Leu Phe Leu Ala Arg Tyr Gly Leu Ala
                565                    570                    575

Leu Glu Lys Ala Gly Lys Tyr Arg Val Arg Leu Arg Tyr Ala Thr Asp
                580                    585                    590

Ala Asp Ile Val Leu His Val Asn Asp Ala Gln Ile Gln Met Pro Lys
            595                    600                    605

Thr Met Asn Pro Gly Glu Asp Leu Thr Ser Lys Thr Phe Lys Val Ala
        610                    615                    620

Asp Ala Ile Thr Thr Val Asn Leu Ala Thr Asp Ser Ser Val Ala Val
625                     630                    635                    640

Lys His Asn Val Gly Glu Asp Pro Asn Ser Thr Leu Ser Gly Ile Val
                645                    650                    655

Tyr Val Asp Arg Ile Glu Phe Ile Pro Val Asp Glu Thr Tyr Glu Ala
                660                    665                    670

Glu
```